(12) United States Patent
Abdelgany et al.

(10) Patent No.: US 7,763,057 B2
(45) Date of Patent: *Jul. 27, 2010

(54) BIASED ANGLE POLYAXIAL PEDICLE SCREW ASSEMBLY

(75) Inventors: Mahmoud F. Abdelgany, Rockaway, NJ (US); Aaron D. Markworth, Saddle Brook, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 822 days.

This patent is subject to a terminal disclaimer.

(21) Appl. No.: 11/564,972

(22) Filed: Nov. 30, 2006

(65) Prior Publication Data

US 2007/0093831 A1      Apr. 26, 2007

Related U.S. Application Data

(63) Continuation of application No. 11/048,213, filed on Feb. 1, 2005, now Pat. No. 7,163,539.

(60) Provisional application No. 60/548,543, filed on Feb. 27, 2004, provisional application No. 60/622,454, filed on Oct. 27, 2004.

(51) Int. Cl.
    *A61B 17/04*       (2006.01)
(52) U.S. Cl. ................. 606/305; 606/306; 606/308; 606/266; 606/272
(58) Field of Classification Search ............ 606/60, 606/264–279, 300–320
    See application file for complete search history.

(56) References Cited

U.S. PATENT DOCUMENTS

| | | | |
|---|---|---|---|
| 3,054,321 A * | 9/1962 | Macchia | ............ 411/403 |
| 4,887,596 A | 12/1989 | Sherman | |
| 4,946,458 A | 8/1990 | Harms et al. | |
| 5,067,955 A | 11/1991 | Cotrel | |
| 5,129,388 A | 7/1992 | Vignaud et al. | |
| 5,246,442 A | 9/1993 | Ashman et al. | |
| 5,360,431 A | 11/1994 | Puno et al. | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,476,464 A | 12/1995 | Metz-Stavenhagen et al. | |
| 5,520,689 A | 5/1996 | Schlapfer et al. | |
| 5,536,268 A | 7/1996 | Griss | |
| 5,545,165 A | 8/1996 | Biedermann et al. | |
| 5,669,911 A | 9/1997 | Errico et al. | |

(Continued)

FOREIGN PATENT DOCUMENTS

DE            19950075 A1 *   4/2001

(Continued)

*Primary Examiner*—Eduardo C Robert
*Assistant Examiner*—Lynnsy Schneider
(74) *Attorney, Agent, or Firm*—Rahman LLC

(57) ABSTRACT

A pedicle screw assembly and method of assembly comprises a longitudinal member; a screw head comprising a bulbous end, wherein the screw head has a slot adapted to receive the longitudinal member; a bone fixator component comprising a concave socket having a biased angled top and a rounded bottom adapted to receive the screw head; a locking pin adapted to engage the screw head, the bone fixator component, and the longitudinal member; and a blocker adapted to engage the screw head and to secure the longitudinal member. Additionally, the bone fixator component may be configured as any of a bone screw and a hook.

19 Claims, 24 Drawing Sheets

U.S. PATENT DOCUMENTS

| | | | |
|---|---|---|---|
| 5,672,176 | A | 9/1997 | Biedermann et al. |
| 5,733,286 | A | 3/1998 | Errico et al. |
| 5,735,851 | A * | 4/1998 | Errico et al. ............ 606/266 |
| 5,752,957 | A * | 5/1998 | Ralph et al. ............ 606/266 |
| 5,863,293 | A | 1/1999 | Richelsoph |
| 5,879,350 | A | 3/1999 | Sherman et al. |
| 5,882,350 | A | 3/1999 | Ralph et al. |
| 5,885,286 | A | 3/1999 | Sherman et al. |
| 5,951,553 | A | 9/1999 | Betz et al. |
| 5,964,760 | A | 10/1999 | Richelsoph |
| 5,964,767 | A | 10/1999 | Tapia et al. |
| 5,989,250 | A * | 11/1999 | Wagner et al. ............ 606/250 |
| 6,022,350 | A | 2/2000 | Ganem |
| 6,030,389 | A * | 2/2000 | Wagner et al. ............ 606/71 |
| 6,045,579 | A | 4/2000 | Hochshuler et al. |
| 6,053,917 | A | 4/2000 | Sherman et al. |
| 6,063,090 | A | 5/2000 | Schlapfer |
| 6,074,391 | A | 6/2000 | Metz-Stavenhagen et al. |
| 6,077,262 | A | 6/2000 | Schlapfer et al. |
| 6,090,110 | A | 7/2000 | Metz-Stavenhagen |
| 6,090,111 | A | 7/2000 | Nichols |
| 6,113,601 | A | 9/2000 | Tatar |
| 6,132,430 | A | 10/2000 | Wagner |
| 6,132,432 | A | 10/2000 | Richelsoph |
| 6,187,005 | B1 | 2/2001 | Brace et al. |
| 6,248,105 | B1 | 6/2001 | Schlapfer et al. |
| 6,273,888 | B1 | 8/2001 | Justis |
| 6,280,442 | B1 | 8/2001 | Barker et al. |
| 6,290,703 | B1 | 9/2001 | Ganem |
| 6,302,888 | B1 | 10/2001 | Mellinger et al. |
| RE37,665 | E | 4/2002 | Ralph et al. |
| 6,368,321 | B1 | 4/2002 | Jackson |
| 6,371,957 | B1 | 4/2002 | Amrein et al. |
| 6,416,515 | B1 | 7/2002 | Wagner |
| 6,454,769 | B2 | 9/2002 | Wagner et al. |
| 6,475,218 | B2 | 11/2002 | Gournay et al. |
| 6,485,491 | B1 | 11/2002 | Farris et al. |
| 6,485,492 | B1 | 11/2002 | Halm et al. |
| 6,488,681 | B2 | 12/2002 | Martin et al. |
| 6,554,834 | B1 * | 4/2003 | Crozet et al. ............ 606/65 |
| 6,562,040 | B1 | 5/2003 | Wagner |
| 6,565,565 | B1 | 5/2003 | Yuan et al. |
| 6,595,992 | B1 | 7/2003 | Wagner et al. |
| 6,610,063 | B2 | 8/2003 | Kumar et al. |
| 6,613,050 | B1 | 9/2003 | Wagner et al. |
| 6,623,485 | B2 | 9/2003 | Doubler et al. |
| 6,641,586 | B2 | 11/2003 | Varieur |
| 6,648,888 | B1 | 11/2003 | Shluzas |
| 6,660,004 | B2 | 12/2003 | Barker et al. |
| 6,736,820 | B2 | 5/2004 | Biedermann et al. |
| 6,780,186 | B2 | 8/2004 | Errico et al. |
| 6,858,030 | B2 | 2/2005 | Martin et al. |
| 6,890,334 | B2 * | 5/2005 | Brace et al. ............ 606/281 |
| 6,974,460 | B2 | 12/2005 | Carbone et al. |
| 7,022,122 | B2 | 4/2006 | Amrein et al. |
| RE39,089 | E | 5/2006 | Ralph et al. |
| 7,118,571 | B2 | 10/2006 | Kumar et al. |
| 7,128,743 | B2 | 10/2006 | Metz-Stavenhagen |
| 7,524,326 | B2 * | 4/2009 | Dierks ............ 606/308 |
| 2003/0055426 | A1 | 3/2003 | Carbone et al. |
| 2003/0073996 | A1 | 4/2003 | Coubler et al. |
| 2003/0163133 | A1 * | 8/2003 | Altarac et al. ............ 606/61 |
| 2004/0153077 | A1 | 8/2004 | Biedermann et al. |

FOREIGN PATENT DOCUMENTS

| | | |
|---|---|---|
| EP | 1090595 A2 | 4/2001 |
| EP | 1254640 A2 | 11/2002 |
| EP | 1293168 A2 | 3/2003 |
| WO | WO9834554 | 8/1998 |
| WO | WO9955246 A1 | 11/1999 |
| WO | WO0122893 A1 | 4/2001 |
| WO | WO03068088 A1 | 8/2003 |

* cited by examiner

SECTION X-X

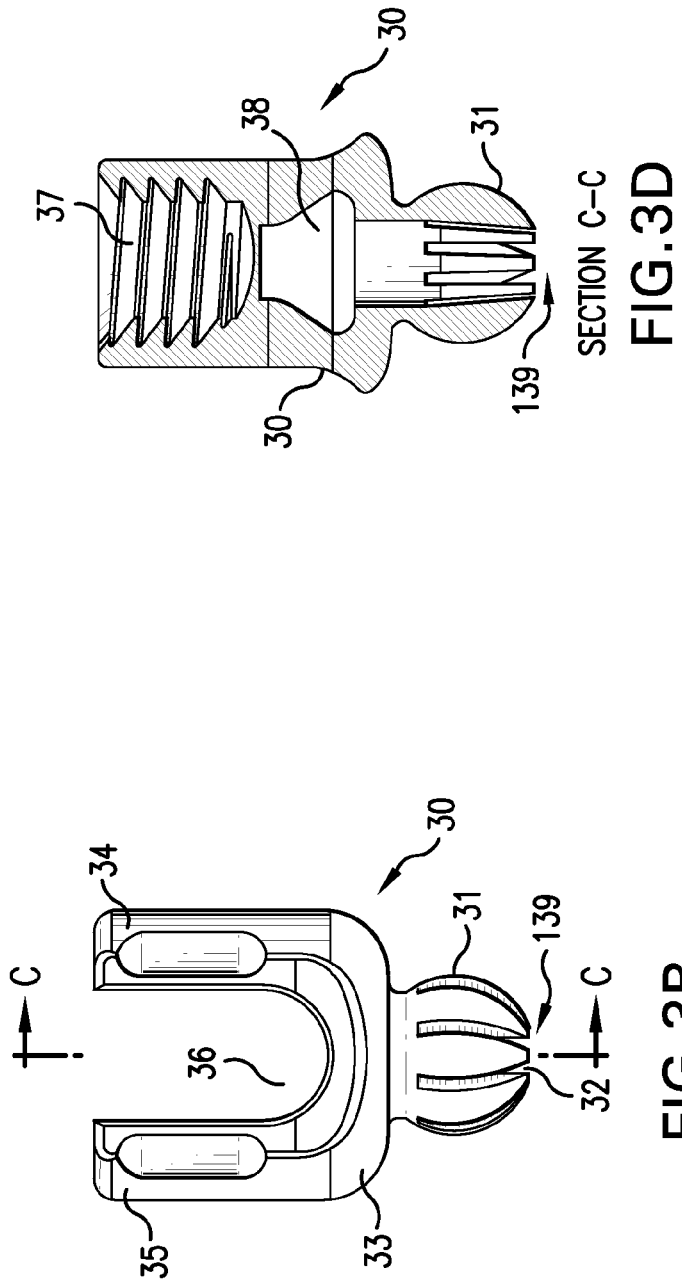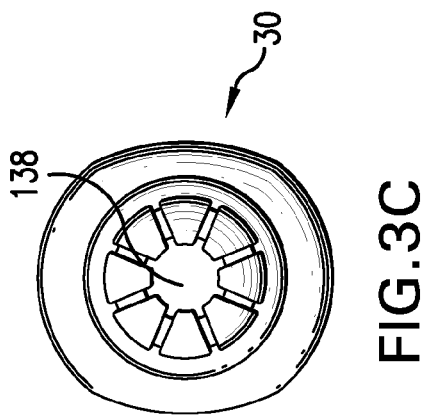

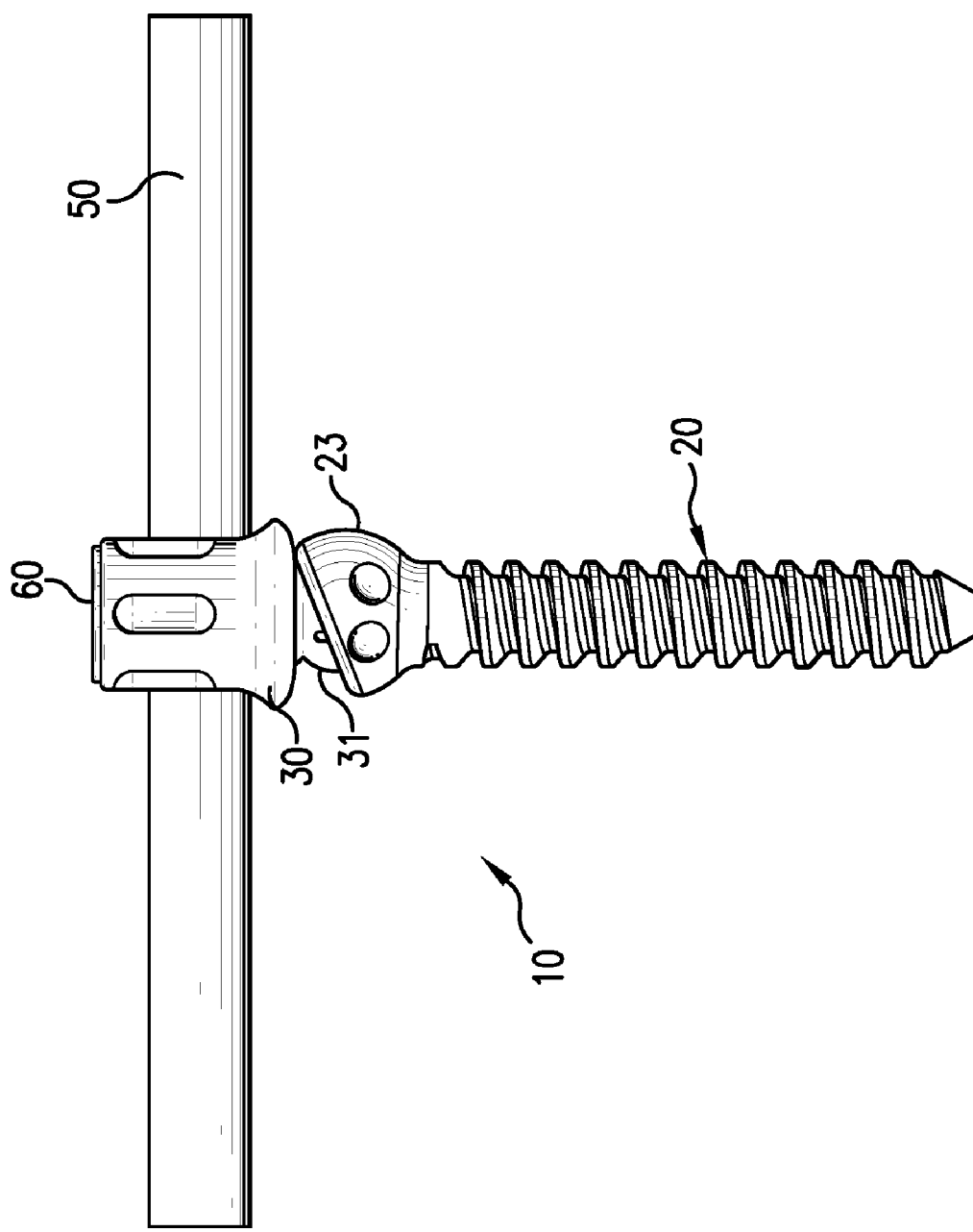

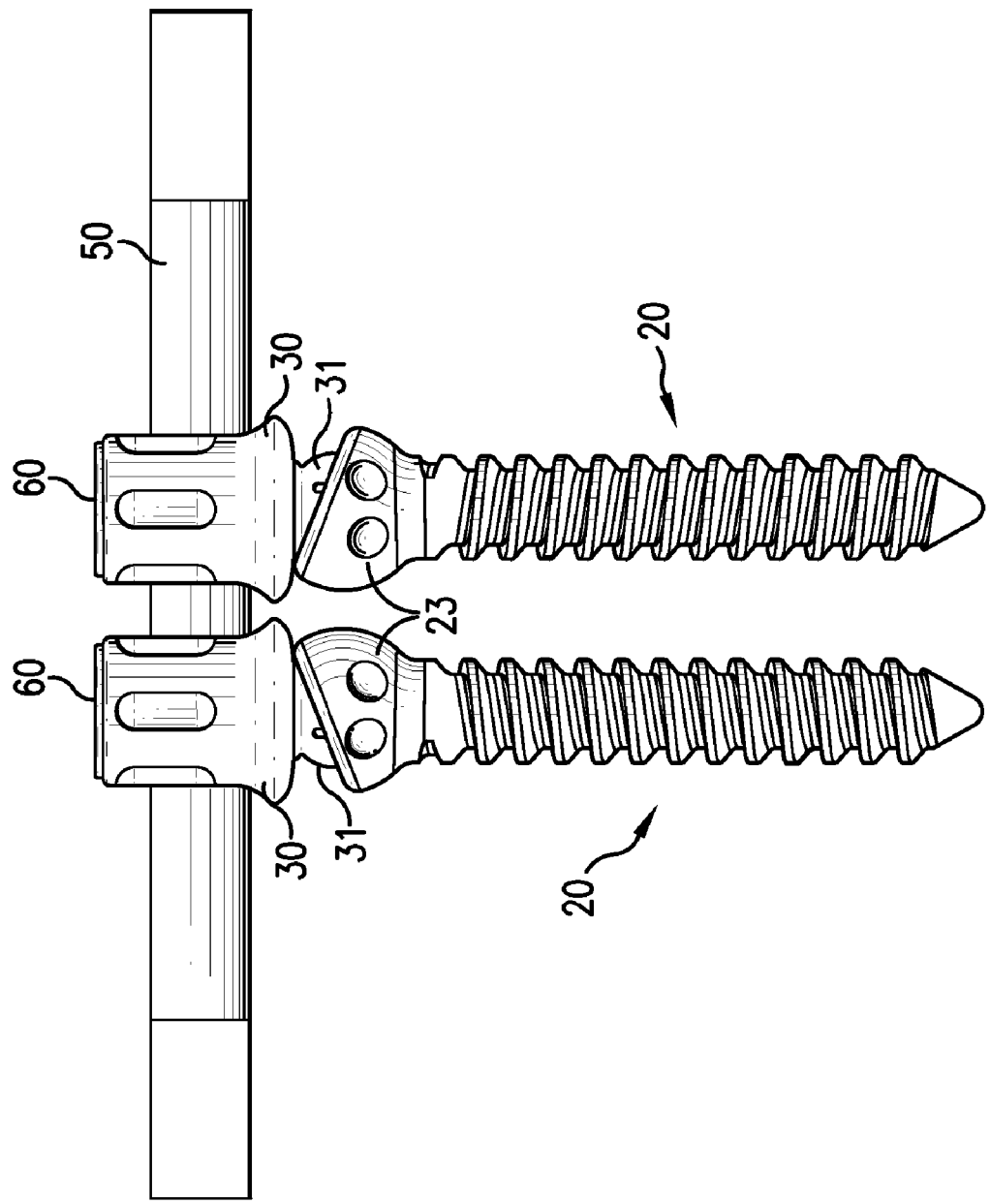

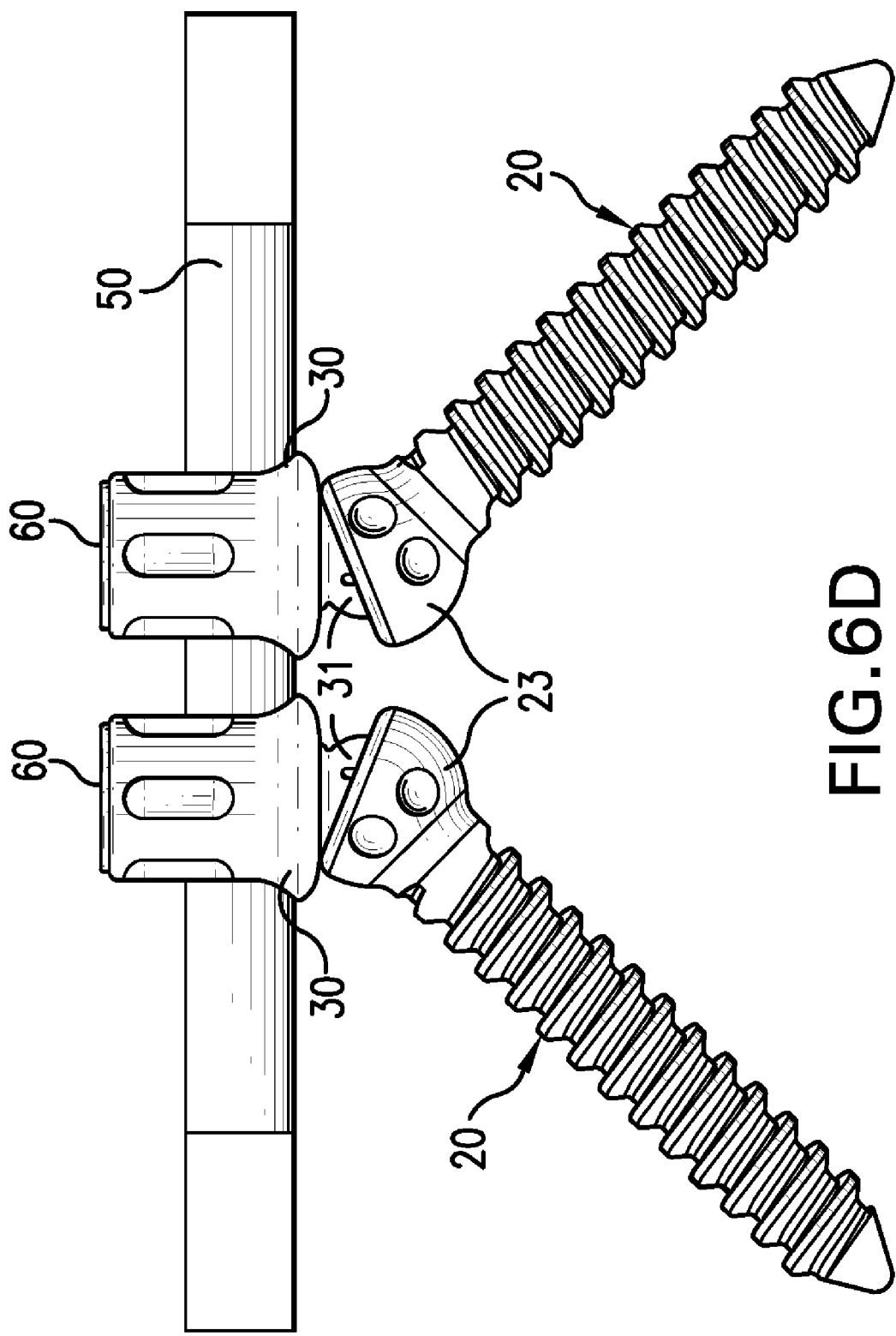

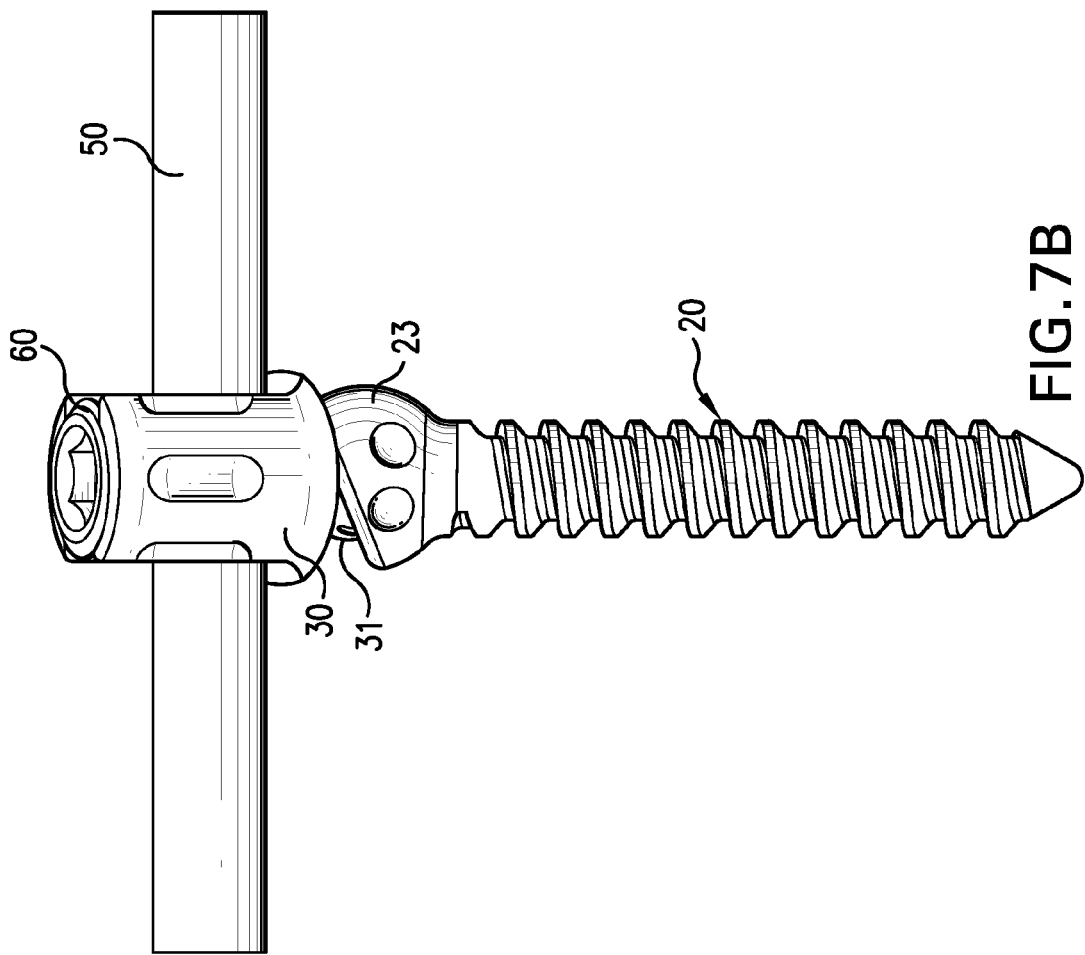
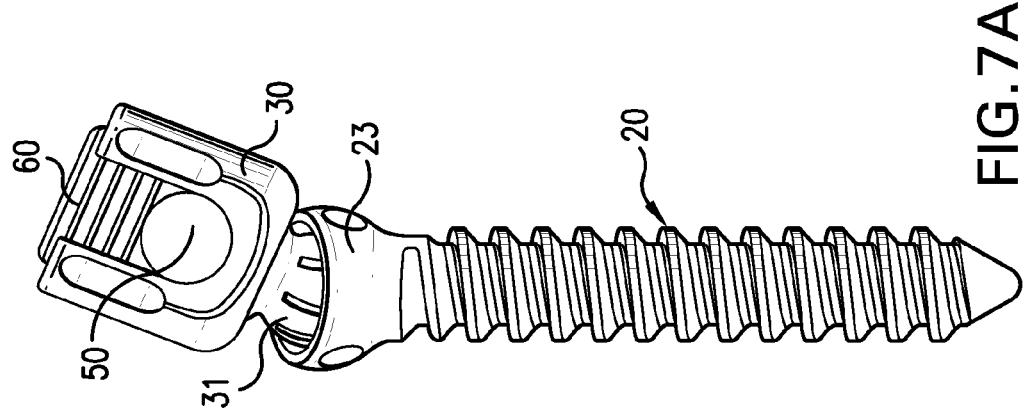
FIG. 7B
FIG. 7A

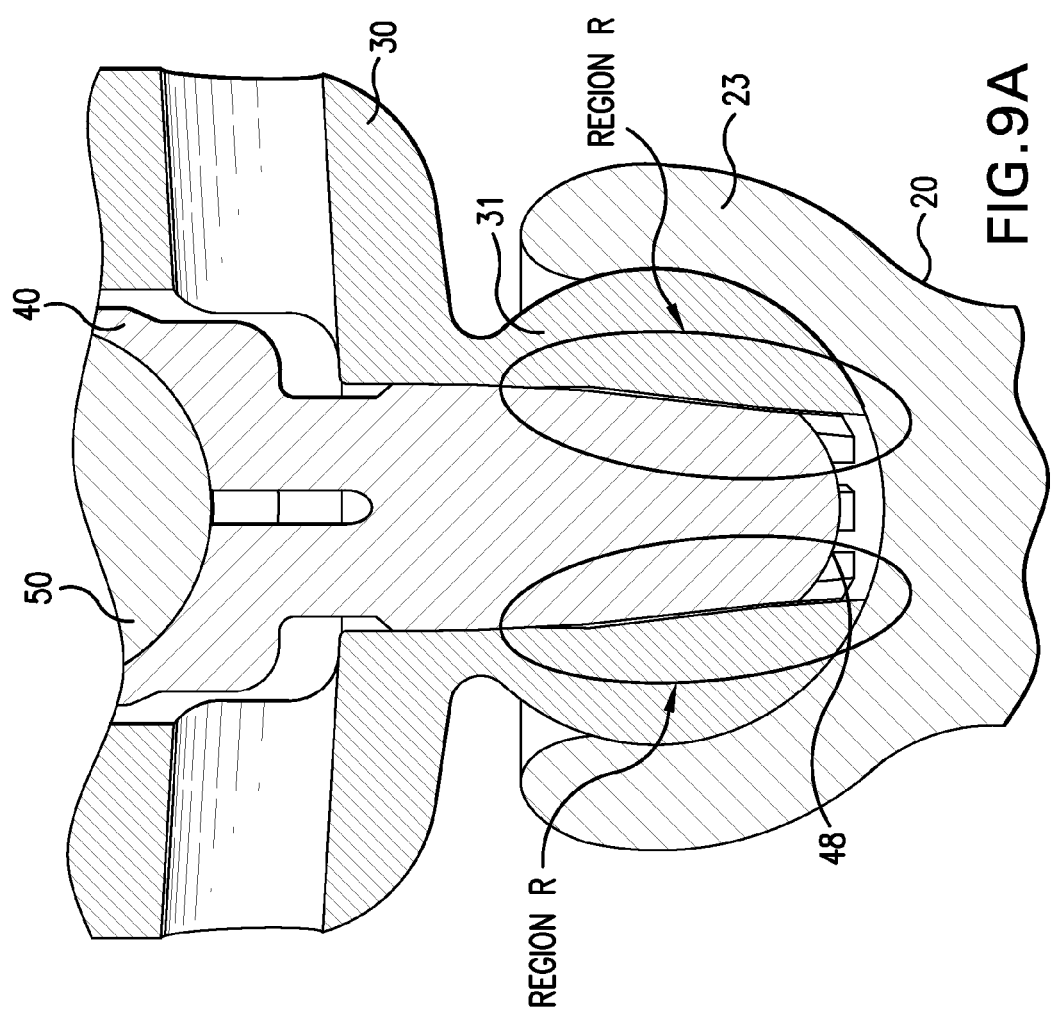

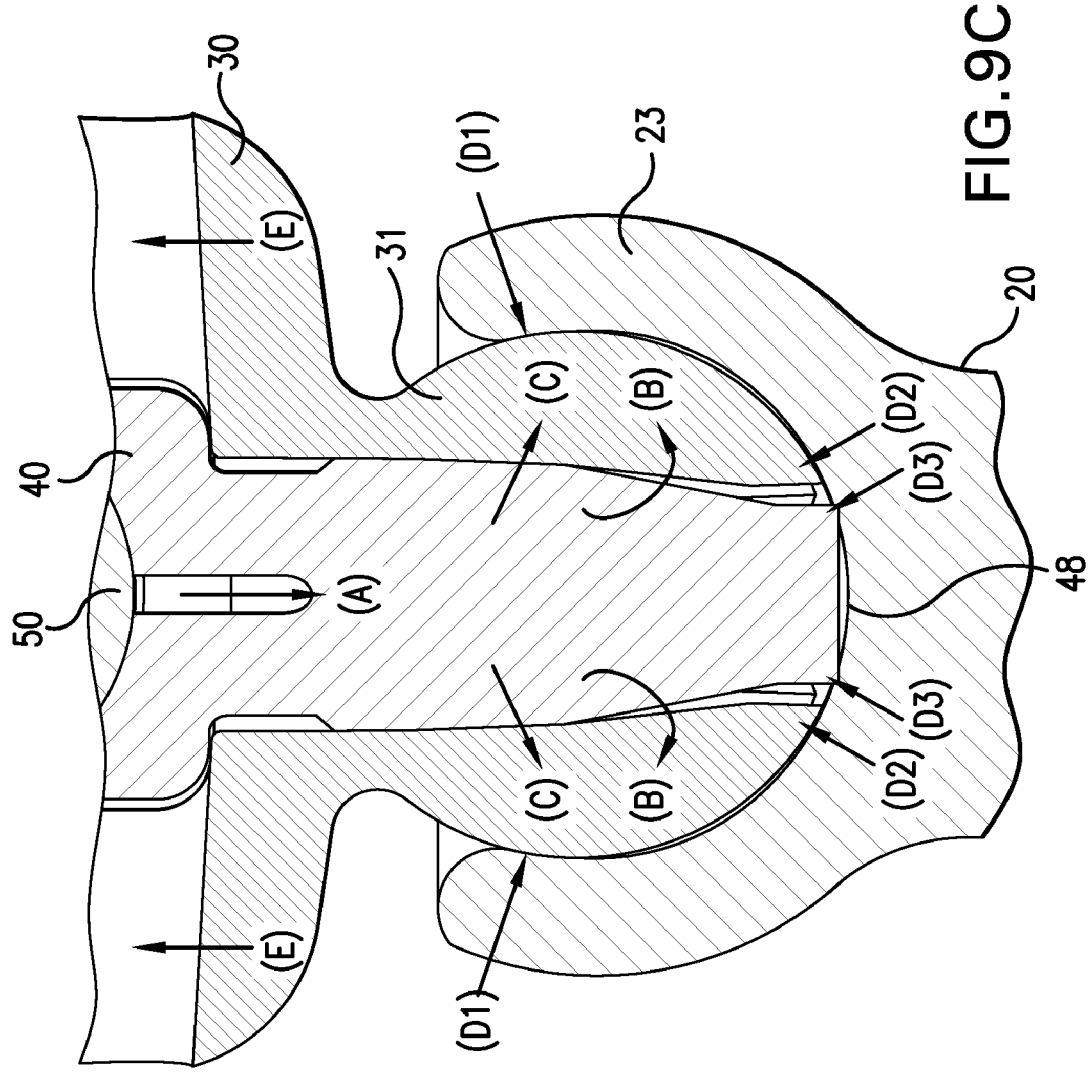

BIASED ANGLE POLYAXIAL PEDICLE SCREW ASSEMBLY

CROSS REFERENCE TO RELATED APPLICATION

This application is a continuation of U.S. application Ser. No. 11/048,213 filed Feb. 1, 2005 now U.S. Pat. No. 7,163,539 which claims the benefit of U.S. Provisional Patent Application No. 60/548,543 filed on Feb. 27, 2004 and U.S. Provisional Patent Application No. 60/622,454 filed on Oct. 27, 2004, the contents of which in their entireties are herein incorporated by reference.

BACKGROUND OF THE INVENTION

1. Field of the Invention

The embodiments of the invention generally relate to medical devices and assemblies, and more particularly to an orthopedic surgical implant assembly used in the field of surgical lumbar, thoracic, and cervical spine treatment.

2. Description of the Related Art

Surgical procedures treating spinal injuries are one of the most complex and challenging surgeries for both the patient and the surgeon. When there are various deformities, trauma, or fractures of the vertebra, surgeons may attempt to "fuse" them together by attaching screw-like devices into the pedicles of the spine and thereby connecting several vertebrae (typically two or more) using a semi-rigid rod. However, due to the complexity of the human anatomy, most surgeons must bend the rod (causing notches thereby reducing fatigue resistance) before placing them into two or more non-aligned pedicle screws that vary in height in order to properly stabilize the pedicle screw assembly within the patient's body. However, this bending causes notches and reduces fatigue resistance and wastes valuable surgery time before the surgeon is able to insert the rod. That is, the surgeon must sacrifice the freedom of optimal screw placement in the spine for ease of construct assembly.

Most conventional polyaxial screw systems generally consist of a bone screw with the top portion of that screw pivoting inside a screw head. This typical conventional design necessitates the bones screw to have a narrow neck just below the entrance to the bottom of the screw head. This allows clearance for the polyaxiality motion of the screw construct. However, this smaller and weaker neck portion is significantly further away from the forces being applied through the rod, which consequently allows a bigger moment arm and increases the chance of screw breakage at the weak neck portion.

Depending on the purpose of the spine surgery, indications, and patient size, surgeons must pre-operatively choose between different spinal systems with differing rod sizes pre-operatively sometimes causing delays in surgery while waiting for more adequate systems to be sterilized. Most conventional systems depend on deformation and notching of the rod to be able to lock it into the screw head. This tends to significantly reduce the fatigue life of the rod. Some surgeons prefer monoaxial screws for rigidity, while some sacrifice rigidity for surgical flexibility in screw placement. Therefore, a system is needed to accommodate both theories. For example, during scoliosis surgery conventional polyaxial systems typically cannot lock into a desired position to persuade the spinal column into the desired correction before final construct assembly.

Most conventional top loading polyaxial spine screws address cantilever failure by utilizing too much stress to the constructs making them weaker in other areas of concern. Moreover, most conventional polyaxial screws do not generally offer enough medial/lateral flexibility because the rod sits too closely on top of the center of rotation of the bone screw producing a smaller arc of rotation. Furthermore, most conventional titanium top loading screw systems only accommodate one rod size. Additionally, most conventional spinal implant designs can only accommodate either a monoaxial design or, separately, a polyaxial design, but not in one assembly. As such, most conventional screw assemblies cannot accommodate 3, 3.25, 3.5, and 4 mm rod sizes in one singular screw assembly. Typically, the particular size of rod used depends on the patient's size and other factors, which may not be determined until after the surgery begins and, potentially, only after the surgeon has already inserted the bone screw into the bone.

Generally, most conventional top loading polyaxial spine screws do not do enough to address cantilever failure of the assembly components. Additionally, most polyaxial screws generally do not offer enough flexibility because the rod sits too closely on top of the center of rotation of the bone screw producing a smaller arc of rotation. Furthermore, most conventional top loading screw systems generally do not accommodate different rod sizes. Moreover, most conventional polyaxial screws offer an equal degree of rotation or freedom referenced to the main screw axis. However, some portions of the spine do not need the system to provide equal polyaxial motion in all directions. For example, some portions of the spine require a range of 5 degrees in one direction and 45 degrees in the opposite direction on the same plane. Generally, most conventional systems simply provide 25 degrees all around. Thus, there remains a need for a new and improved pedicle screw assembly capable of overcoming the limitations of the conventional designs thereby providing the surgeon with improved intra-operative flexibility and the patient with an improved prognosis for better and complete rehabilitation.

SUMMARY OF THE INVENTION

In view of the foregoing, an embodiment of the invention provides a pedicle screw assembly comprising a screw head comprising a bulbous end; a bone fixator component comprising an angled concave socket adapted to receive the bulbous end of the screw head; a pin mounted in the screw head; and a blocker adapted to engage the screw head. The screw head comprises a slot adapted to receive a longitudinal member. Moreover, the concave socket of the bone fixator component comprises an angled top and a rounded bottom. Preferably, the concave socket of the bone fixator component comprises an inner portion adapted to receive the bulbous end of the screw head; and a dimpled outer portion.

Additionally, the pin is preferably adapted to engage the bone fixator component and the longitudinal member, and the blocker is preferably adapted to secure the longitudinal member. Preferably, the pin comprises an upper saddle portion having a slot and a pair of upright ends; and a lower tapered portion adjacent to the slot. Preferably, the screw head further comprises two opposed upright ends separated by the slot, wherein each of the opposed upright ends comprise an inner wall and an outer wall, wherein the inner wall comprises wall threads, and wherein the outer wall comprises grooves.

Additionally, the blocker preferably comprises blocker threads configured around an outer perimeter of the blocker, the blocker threads being dimensioned and configured to mate with the wall threads. Furthermore, the bulbous end of the screw head may comprise a plurality of slots terminating at an opening at a tip of the bulbous end. Also, the bulbous end of the screw head preferably comprises a hole configured to receive the pin. Moreover, the bone fixator component may comprise any of a bone screw and a hook configuration.

Another aspect of the invention provides a pedicle screw assembly comprising a longitudinal member; a screw head comprising a bulbous end, wherein the screw head has a slot adapted to receive the longitudinal member; a bone fixator component comprising a concave socket having a biased angled top and a rounded bottom adapted to receive the screw head; a locking pin adapted to engage the screw head, the bone fixator component, and the longitudinal member; and a blocker adapted to engage the screw head and to secure the longitudinal member, wherein the concave socket of the bone fixator component preferably comprises an inner portion adapted to receive the bulbous end of the screw head; and a dimpled outer portion. Furthermore, the locking pin preferably comprises an upper saddle portion having a slot and a pair of upright ends; and a lower tapered portion adjacent to the slot. Moreover, the bulbous end of the screw head preferably comprises a hole configured to receive the pin. Additionally, the bone fixator component may comprise any of a bone screw and a hook configuration.

Another embodiment of the invention provides a method of assembling a pedicle screw assembly, wherein the method comprises attaching a screw head comprising a bulbous end to a bone fixator component, wherein the bone fixator component comprises an angled concave socket adapted to receive the bulbous end of the screw head; securing the bone fixator component in a bone; securing a locking pin in the screw head; engaging the saddle pin with the bone fixator component; inserting a longitudinal member in the screw head; and inserting a blocker in the screw head, wherein engagement of the blocker with the screw head causes expansion of the bulbous end of the screw head in the angled concave socket of the bone fixator component.

The embodiments of the invention offer a surgeon more lateral corrective distance than conventional screw assemblies and can accommodate the cervical spine anatomy with a biased angle. The embodiments of the invention may be used as a fixation device in the posterior cervical-thoracic spine.

Additionally, the embodiments of the invention provide an improvement in the field of surgical lumbar and thoracic and cervical spine treatment. The assembly provided by the embodiments of the invention may also be used anteriorly or posteriorly. Furthermore, the assembly provided by the embodiments of the invention may be utilized in surgeries to achieve anterior lumbar interbody fusion, posterior lumbar interbody fusion, transverse lumbar interbody fusion, degenerative disc disease, adult and pediatric scoliosis as a fixation device, and posterior cervical fusion.

These and other aspects of the embodiments of the invention will be better appreciated and understood when considered in conjunction with the following description and the accompanying drawings. It should be understood, however, that the following descriptions, while indicating preferred embodiments of the invention and numerous specific details thereof, are given by way of illustration and not of limitation. Many changes and modifications may be made within the scope of the embodiments of the invention without departing from the spirit thereof, and the embodiments of the invention include all such modifications.

BRIEF DESCRIPTION OF THE DRAWINGS

The embodiments of the invention will be better understood from the following detailed description with reference to the drawings, in which:

FIG. 3(B) illustrates a front view of the screw head of FIG. 3(A) according to an embodiment of the invention;

FIG. 3(C) illustrates a bottom view of the screw head of FIG. 3(A) according to an embodiment of the invention;

FIG. 3(D) illustrates a cross-sectional side view cut along section C-C of the screw head of FIG. 3(B) according to an embodiment of the invention;

FIGS. 6(A) through 6(D) illustrate several views of a fully engaged screw assembly according to an embodiment of the invention;

FIGS. 7(A) through 7(B) illustrate several views of a fully engaged screw assembly in various stages of angulation according to an embodiment of the invention;

FIGS. 9(A) through 9(D) illustrate several cross-sectional views of a screw assembly in various stages of engagement according to an embodiment of the invention.

DETAILED DESCRIPTION OF PREFERRED EMBODIMENTS OF THE INVENTION

Figure 1:
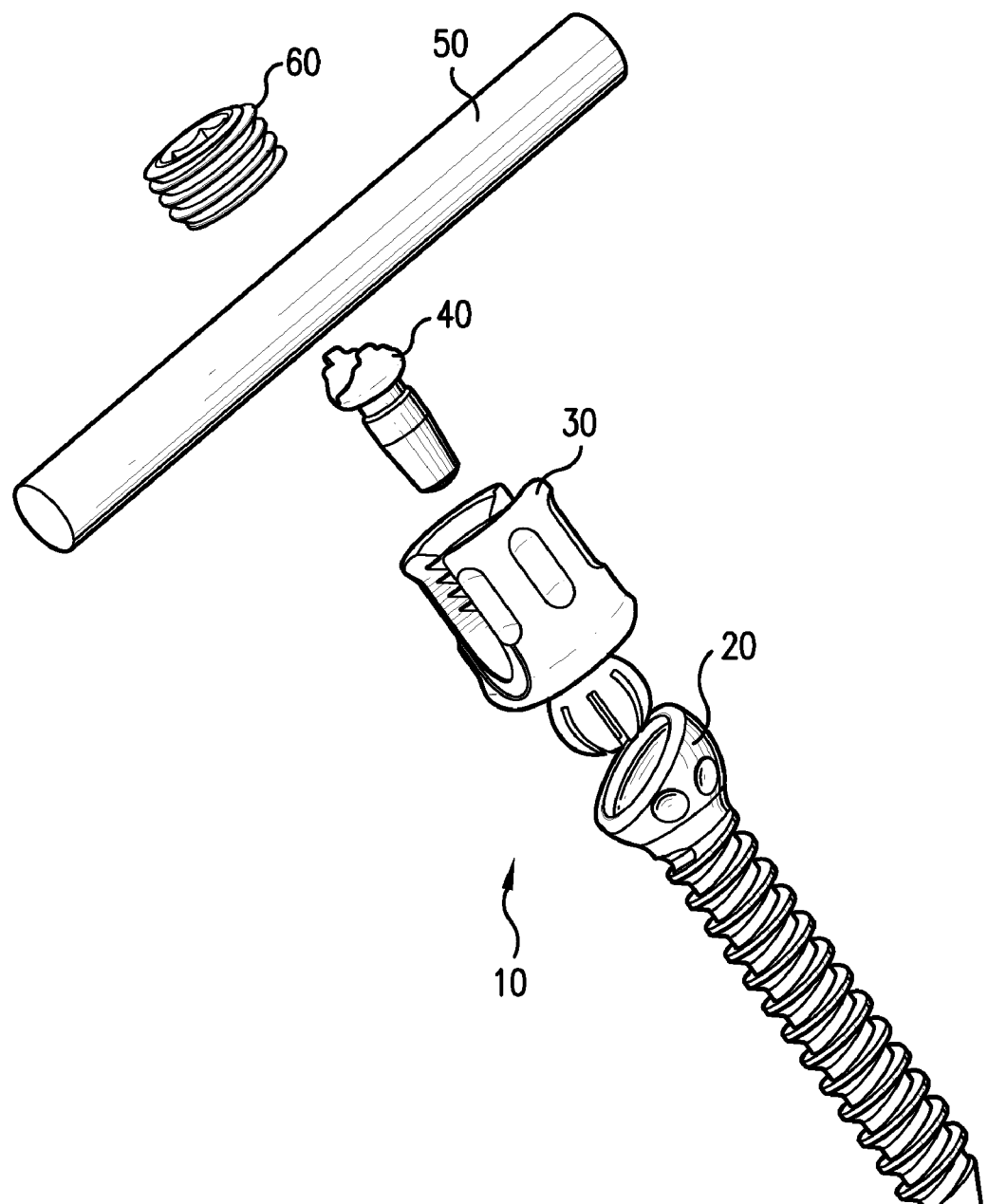
FIG. 1 illustrates an exploded view of the screw assembly according to an embodiment of the invention.

The embodiments of the invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments of the invention. The examples used herein are intended merely to facilitate an understanding of ways in which the embodiments of the invention may be practiced and to further enable those of skill in the art to practice the embodiments of the invention. Accordingly, the examples should not be construed as limiting the scope of the embodiments of the invention.

As mentioned, there remains a need for a new and improved pedicle screw assembly capable of overcoming the limitations of the conventional designs thereby providing the surgeon with improved intra-operative flexibility and the patient with an improved prognosis for better and complete rehabilitation. The embodiments of the invention address this need by providing an improved biased angle polyaxial pedicle screw device and method of assembly capable of offering a surgeon more lateral corrective distance than conventional screw assemblies and accommodating the cervical spine anatomy with a biased angle configuration. Referring now to the drawings and more particularly to FIGS. 1 through 10 where similar reference characters denote corresponding features consistently throughout the figures, there are shown preferred embodiments of the invention.

FIG. 1 illustrates the components of the pedicle screw assembly 10 according to an embodiment of the invention. The assembly 10 shown in FIG. 1 is for a 1-level spinal fixation construct. The bone screw (fixator component) 20, which may be embodied as a screw, hook, or anchor, is pre-assembled at the factory by snapping the screw head 30 into the bone fixator component 20, and then snapping the saddle pin 40 into the screw head 30. This allows the screw head 30 to rotate about the center of rotation freely. This sub-assembly is then inserted and "buried" into the spinal anatomy (not shown) as far as the level of the female dimples 24 (shown in FIG. 2(A)) on the bone fixator component 20. Once all of the needed components are assembled, the bone fixator component 20 is inserted in the spinal anatomy (not shown), the longitudinal member 50, which may be embodied as a rod, bar, plate, etc., is dropped into the screw head 30, and the blocker 60 is used to fixate the construct 10.

The bone fixator component 20 is shown in FIGS. 2(A) through 2(D) (with reference to FIG. 1) with an angled cut on the top socket 23 of the implant and having a generally rounded bottom surface 26. This cut top allows for the screw head 20 to angulate in one direction more than another direction to accommodate the needed extreme angles in the posterior cervical spine. The large angled semi-spherical socket 23 at the top of the bone fixator component 20 acts as the pivot point for the screw head 30. This socket 23 is undercut to accommodate a snap fit in assembly and to prevent unintentional disassembly. The socket 23 includes an inner portion 21 and an outer portion 25, which comprises dimples (or cuts) 24. The female spherical cuts 24 are configured so as to be used by a screwdriver (not shown) to insert the bone fixator component 20 into the patient's spine (not shown).

Figure 2A:
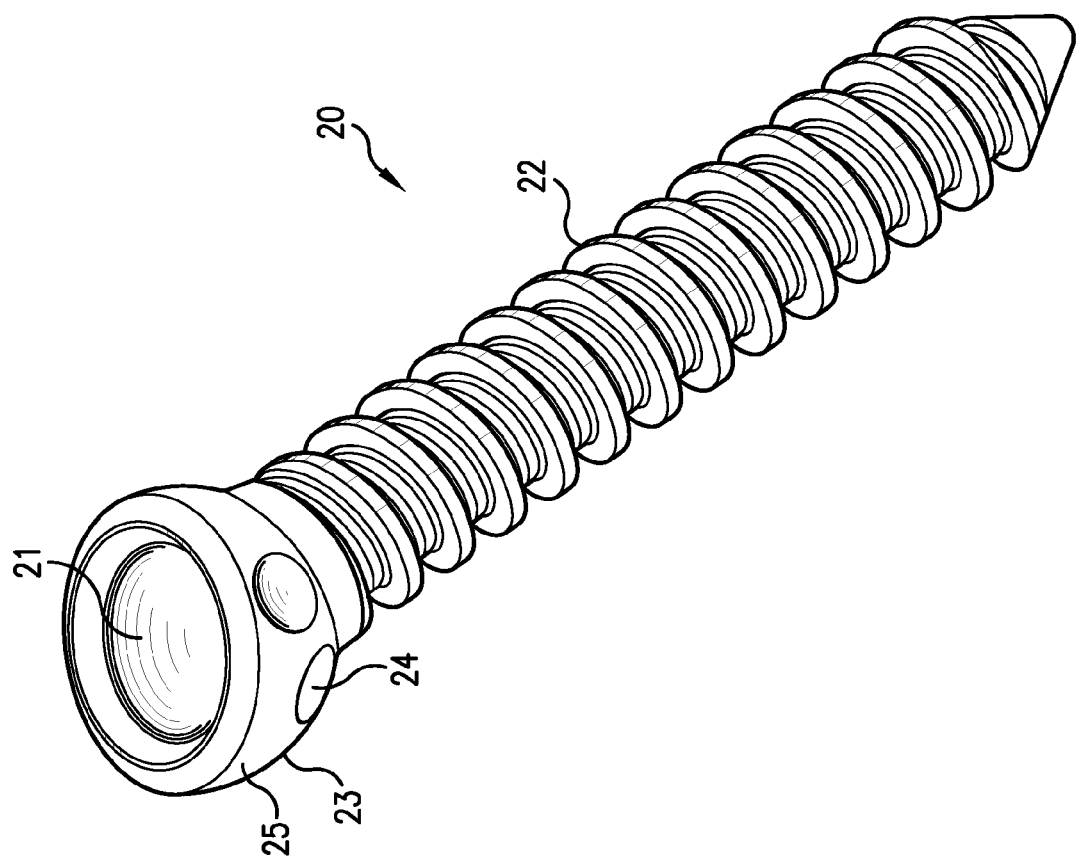
FIG. 2(A) illustrates a perspective view of the bone fixator component of FIG. 1 according to an embodiment of the invention.
Figure 2B:
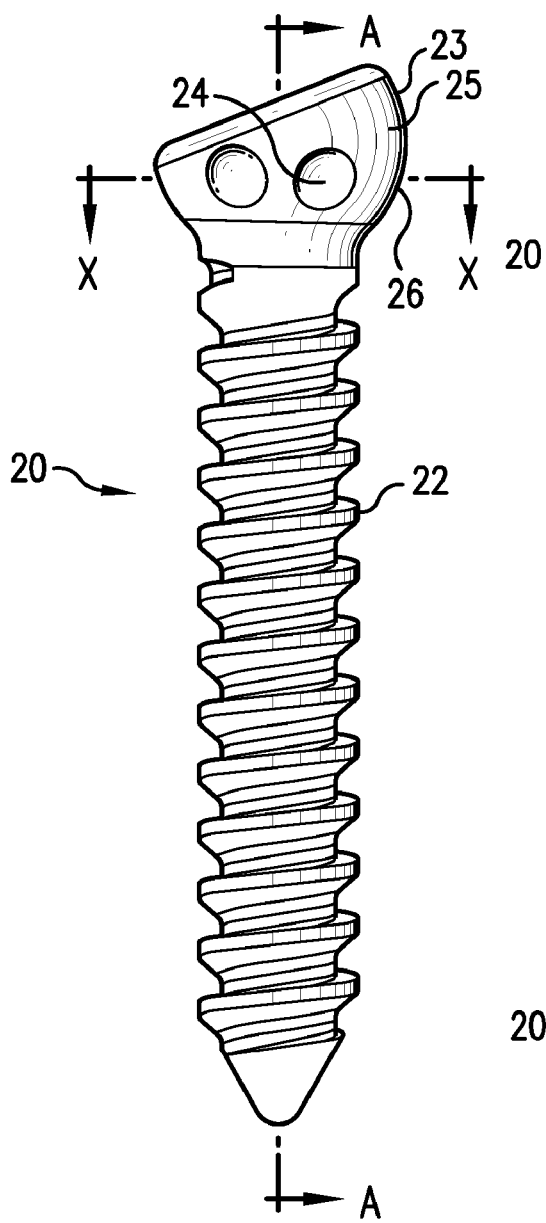
FIG. 2(B) illustrates a front view of the bone fixator component of FIG. 2(A) according to an embodiment of the invention.
Figure 2C:
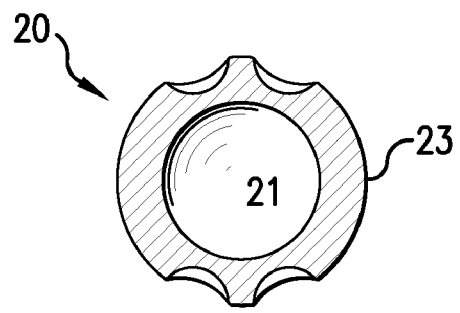
FIG. 2(C) illustrates a cross-sectional top view cut along section X-X of the bone fixator component of FIG. 2(B) according to an embodiment of the invention.
Figure 2D:
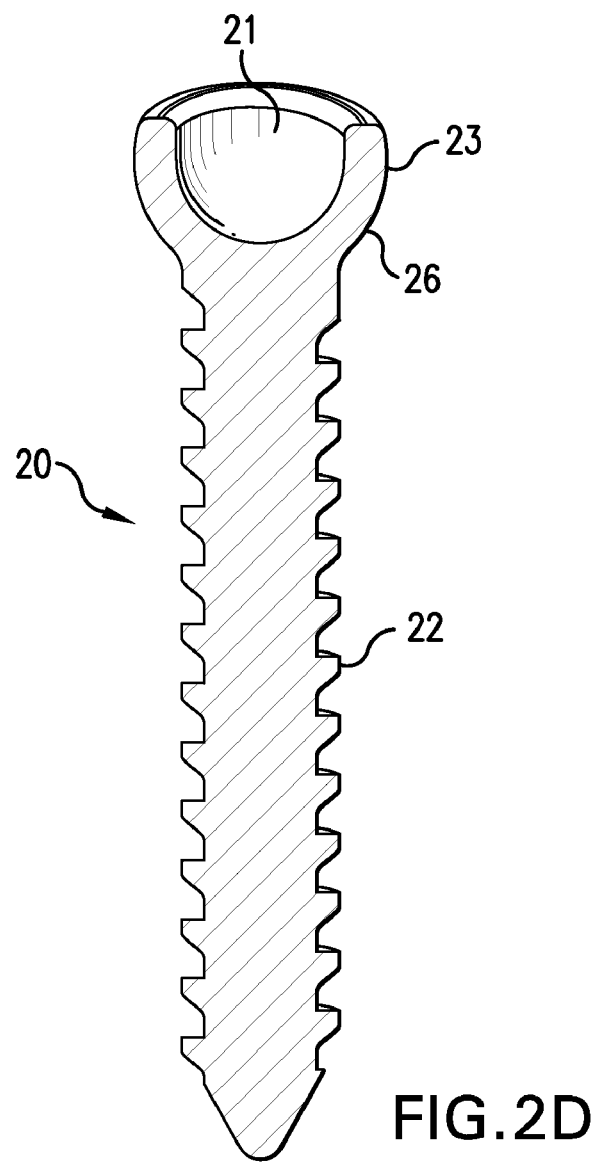
FIG. 2(D) illustrates a cross-sectional side view cut along section A-A of the bone fixator component of FIG. 2(B) according to an embodiment of the invention.
Figure 3A:
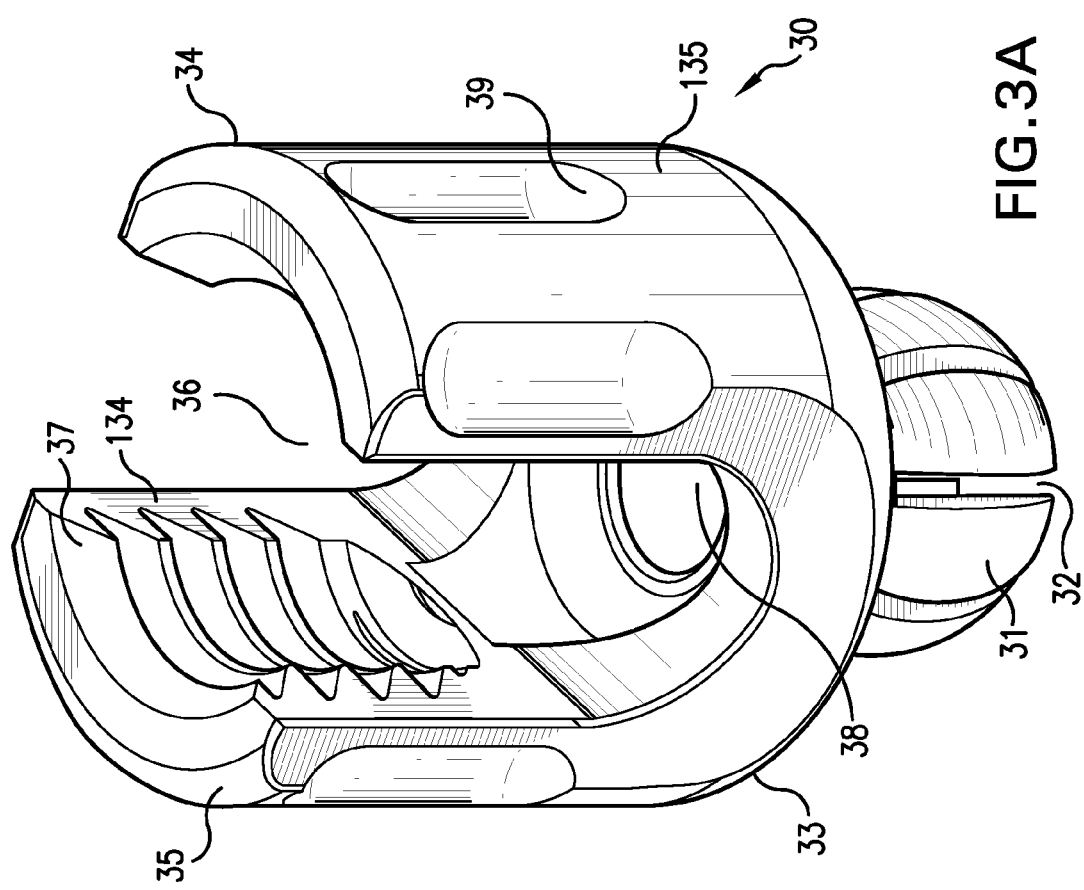
FIG. 3(A) illustrates a perspective view of the screw head of FIG. 1 according to an embodiment of the invention.
Figure 4A:
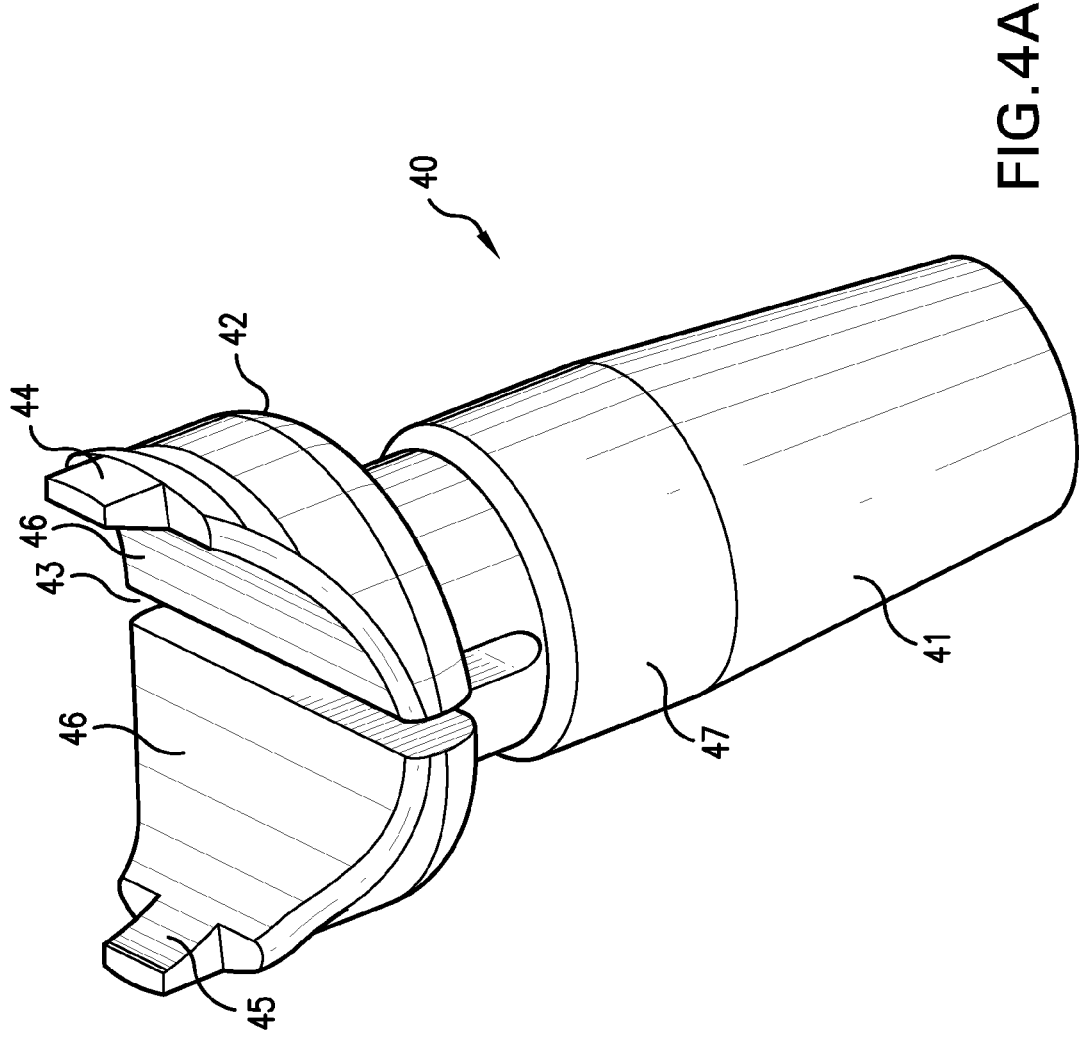
FIG. 4(A) illustrates a perspective view of the saddle pin of FIG. 1 according to an embodiment of the invention.
Figure 4D:
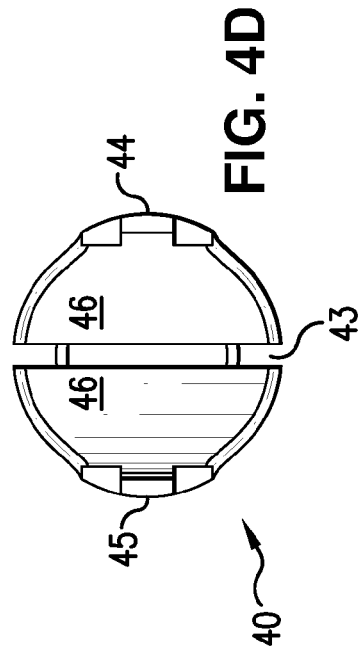
FIG. 4(D) illustrates a top view of the saddle pin of FIG. 4(A) according to an embodiment of the invention.
Figure 4E:
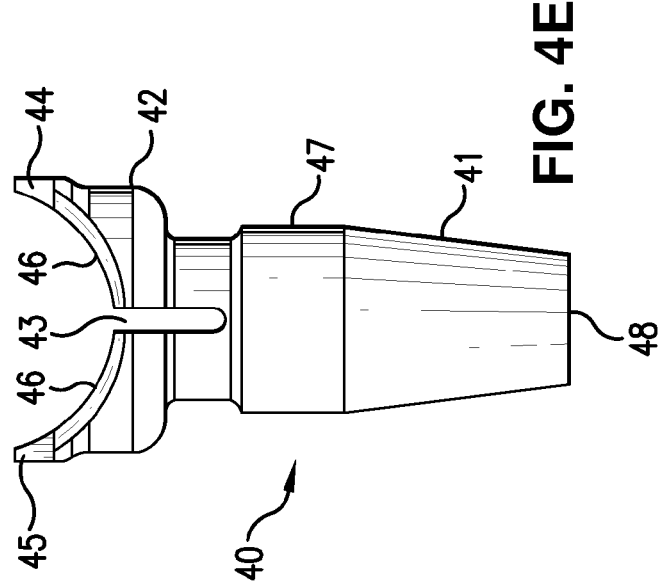
FIG. 4(E) illustrates a front view of the saddle pin of FIG. 4(A) according to an embodiment of the invention.
Figure 4B:
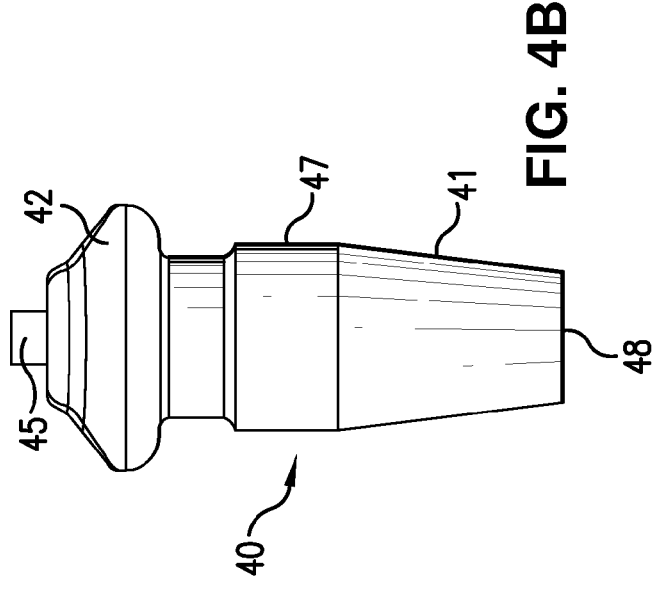
FIG. 4(B) illustrates a side view of the saddle pin of FIG. 4(A) according to an embodiment of the invention.
Figure 4C:
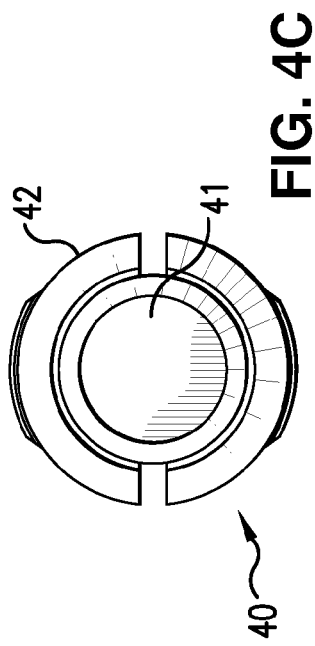
FIG. 4(C) illustrates a bottom view of the saddle pin of FIG. 4(A) according to an embodiment of the invention.

The screw head 30 is shown in FIGS. 3(A) through 3(D) (with reference to FIGS. 1 through 2(D)). At the bottom 139 of the screw head 30 is a male spherical ball 31 that is slotted 32 for assembly purposes and for expansion in the final locking of the construct 10. The male spherical surface 31 can be treated with a rough media to create a rough texture to encourage galling with the inner portion 21 of the large female spherical socket 23 in the bone fixator component 20 (of FIGS. 2(A) through 2(D)). In one embodiment of the invention, there may be a tapered hole 38 inside the male spherical section 31 of the screw head 30 to encourage expansion by the saddle pin 40 (of FIG. 1) as it is driven into its final locking position. The screw head 30 further includes a pair of opposed upright ends 34, 35 separated by a generally U-shaped slotted section 36 adapted to receive the longitudinal member 50. Preferably, the inner wall 134 of the upright ends 34, 35 include threads 37. The indent features 39 on the outside 135 of the screw head 30 are for various instruments (not shown) to manipulate the screw head 30 during surgery.

The saddle pin 40 is illustrated in FIGS. 4(A) through 4(E) (with reference to FIGS. 1 through 3(D)). The saddle pin 40 desirably has a generally rounded upper portion 42 with a generally sloping upper surface 46 on top to allow the use of different size longitudinal members 50 (of FIG. 1) within the same assembly system 10. The upper surface 46 includes a slot 43 that extends down to the lower portion 47 of the saddle pin 40 to accommodate flexibility in the upper portion 42 of the saddle pin 40. The tapered section 41 towards the bottom 47 of the saddle pin 40 can be used to expand and "wedge" the slotted male spherical section 31 of the screw head 30 into the bone fixator component 20 (further shown in FIGS. 8(A) through 8(E)). The bottom tip 48 of the saddle pin 40 can be rounded, flat, or pointed to "dig" in the bone fixator component 20 providing another method of locking the construct other than the wedging effect described above. The two small ears 44, 45 on top of the saddle pin 40 may be used to orient the saddle pin 40 to always accept a longitudinal member 50 within the screw head 30.

Figure 5A:
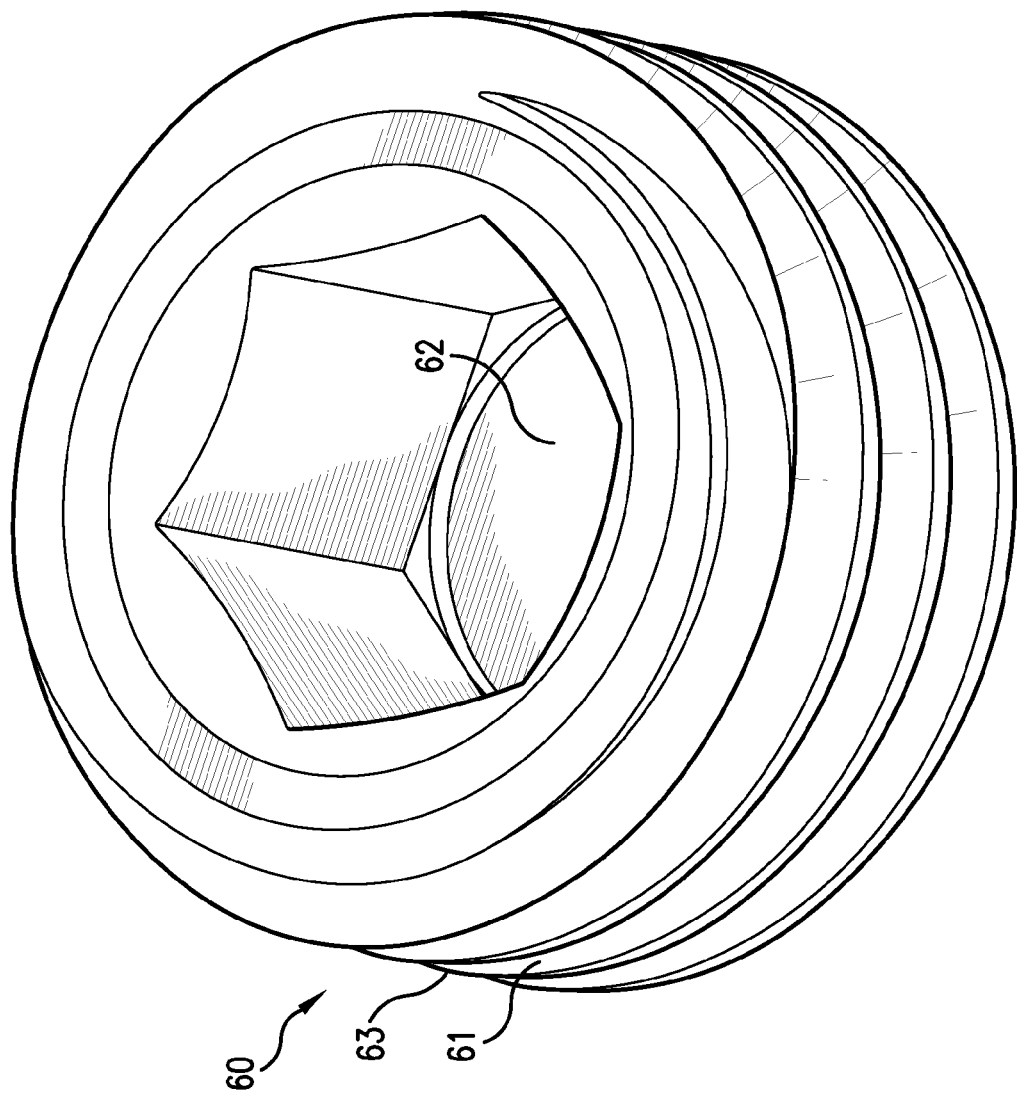
FIG. 5(A) illustrates a perspective view of the blocker of FIG. 1 according to an embodiment of the invention.
Figure 5B:
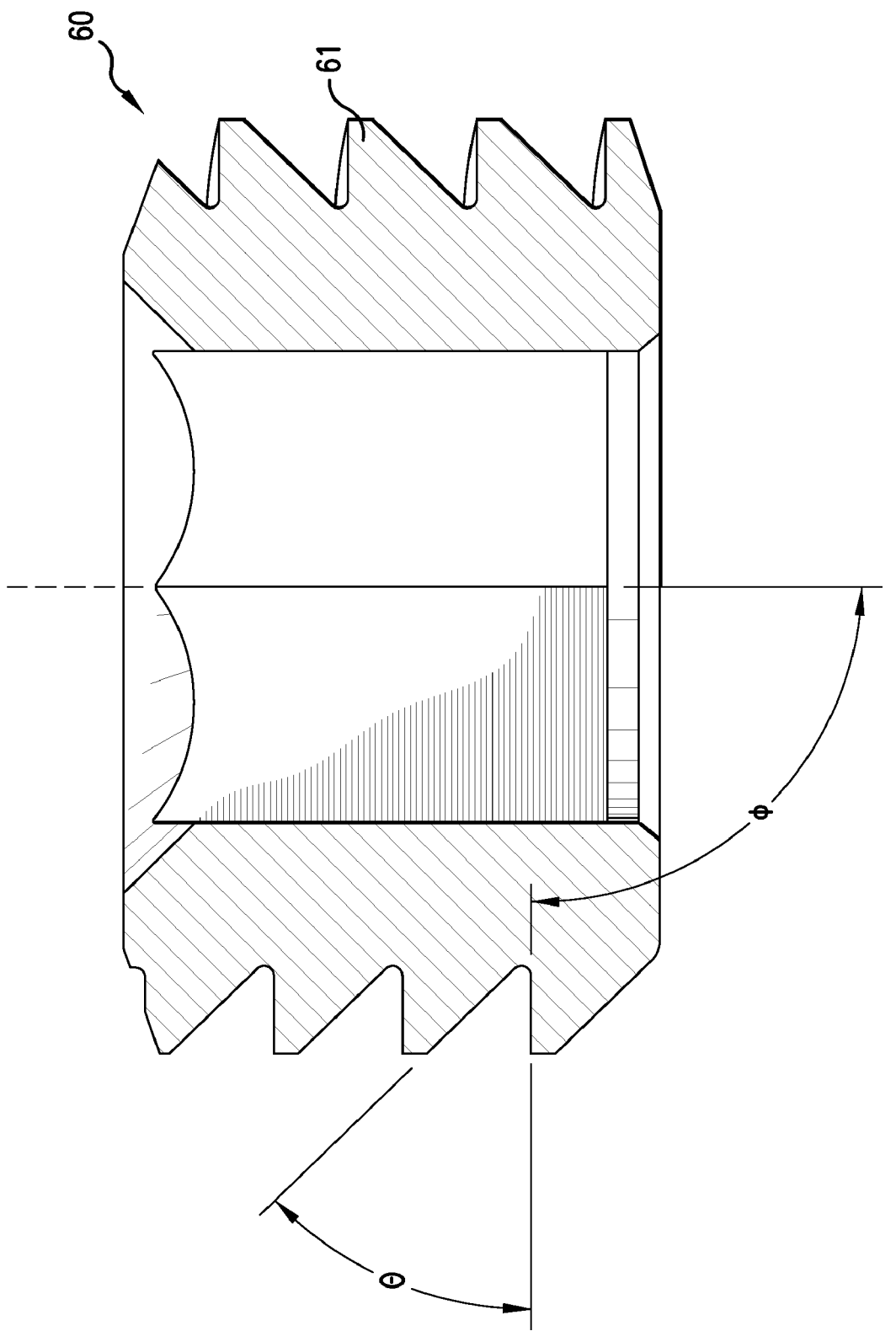
FIG. 5(B) illustrates a cross-sectional side view of the blocker of FIG. 5(A) according to an embodiment of the invention.

FIGS. 5(A) and 5(B) (with reference to FIGS. 1 through 4(E)) illustrate the blocker 60, which is used to push down on the longitudinal member 50 (of FIG. 1) that pushes down onto the saddle pin 40 effectively locking the construct 10. The threads 61 on the blocker 60 are preferably configured around an outer cylindrical perimeter 63 of the blocker 60, and are preferably standard flat buttress threads that are configured to mate with the threads 37 of the screw head 30. Preferably, as shown in FIG. 5(B), the thread angle, θ, equals 45° and φ equals 90°. The flat type "A" buttress threads 61 of the blocker 60 helps prevent the screw head 30 from splaying during final tightening (best seen in FIGS. 8(A) through 8(E)). Preferably, the blocker 60 includes an appropriately sized hex aperture 62 for torque application.

Figure 6B:
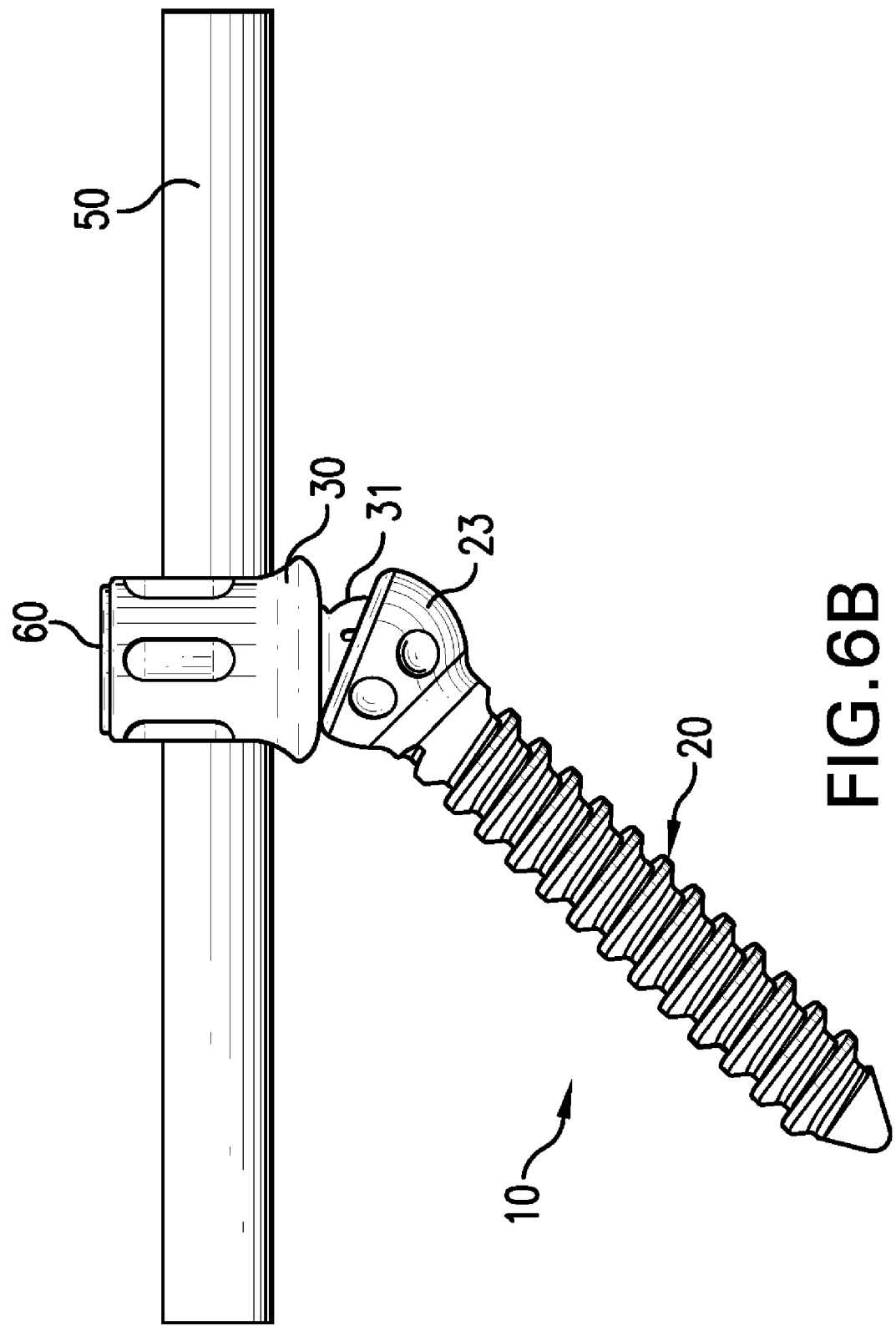

The various angulations scenarios of the fully-assembled screw assembly 10 are shown in FIGS. 6(A) through 7(B). The medial angulation shown in FIGS. 6(A) and 6(B) show an unequal angulation. The medial angulation of the screw head 30 shown in FIG. 7(A) is equal to the medial angulation of the screw head 30 shown in FIG. 7(B). For example, if a system is to accommodate a 60 degree angulation all around the center axis of the bone fixator component 20, it would be a very weak system. When used in the upper thoracic and lower cervical spine, the severe angulation is only needed in the superior inferior direction pointing towards a patient's head (not shown). FIGS. 6(C) and 6(D) illustrate various applications of the screw assembly 10 provided by the embodiments of the invention. As shown, the screw assembly 10 is configured to have flexibility in its design (i.e., angulation).

Figure 8A:
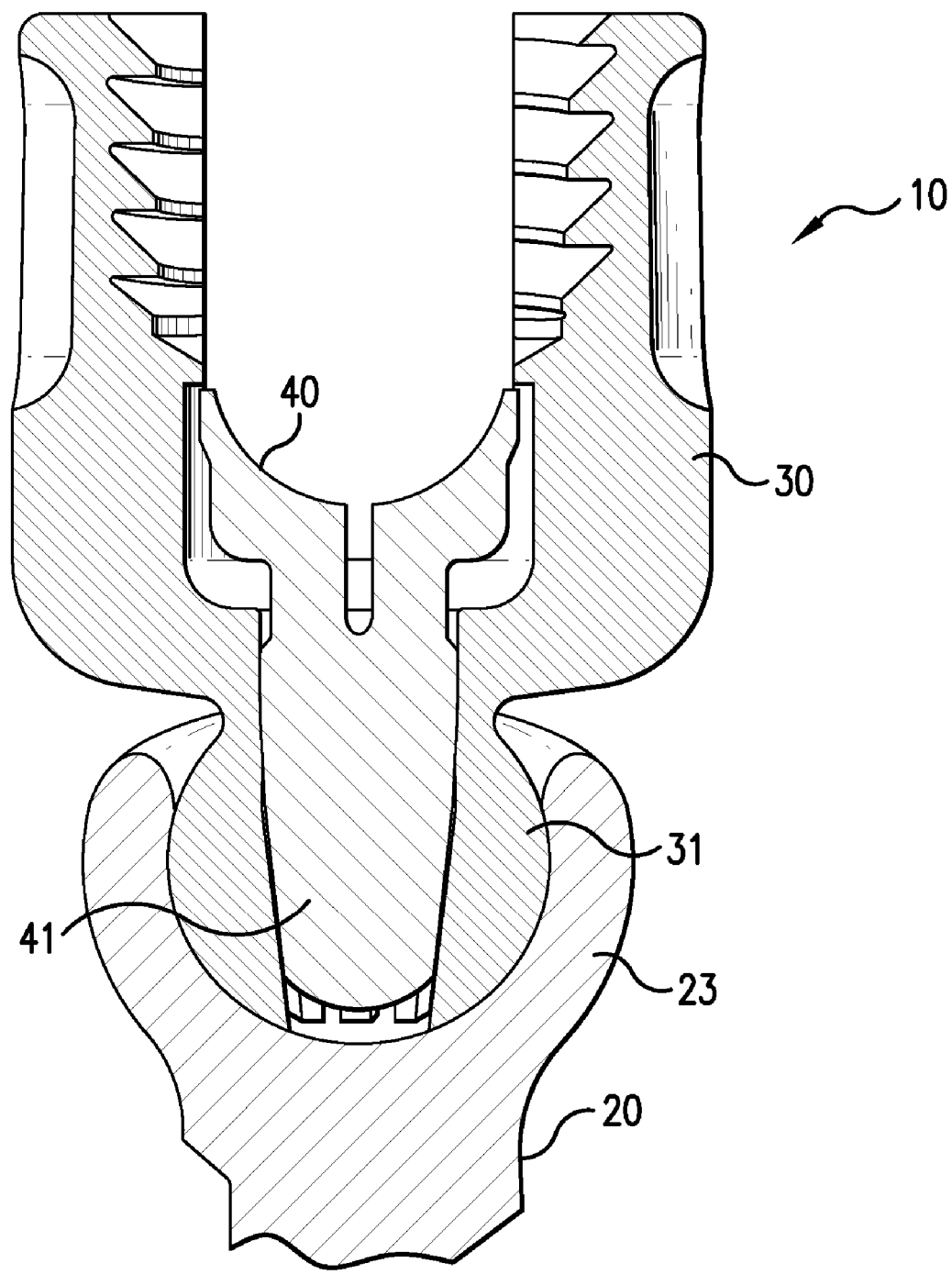
FIGS. 8(A) through 8(E) illustrate several cross-sectional views of a screw assembly in various stages of assembly according to an embodiment of the invention.
Figure 8B:
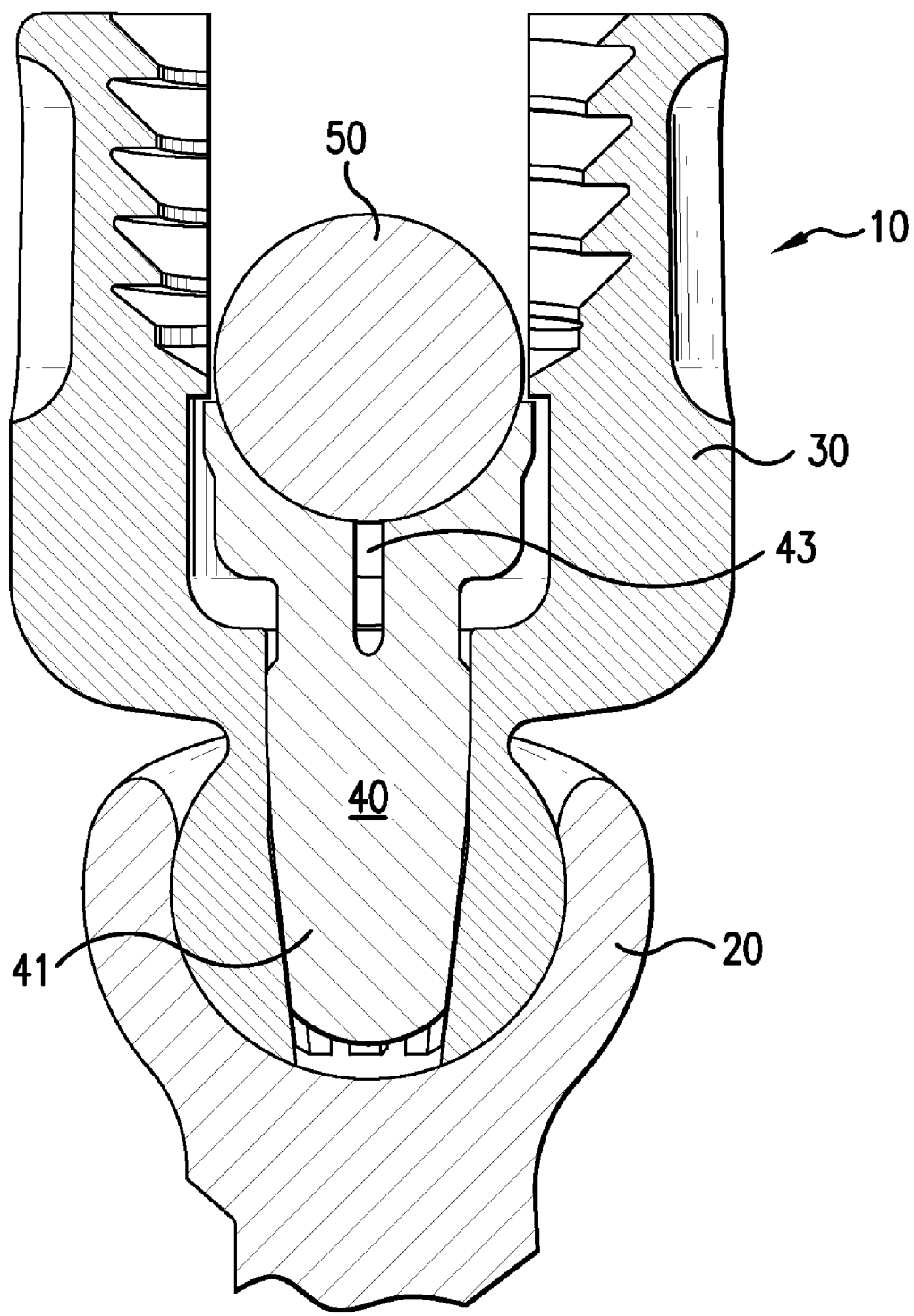

FIGS. 8(A) through 8(E) illustrate cross-sectional views of the assembly 10. The saddle pin 40 cannot escape, fall out or vibrate out of position, and is always oriented to accept a longitudinal member 50. It is shown in FIG. 8(A) that the taper 41 towards the bottom of the saddle pin 40 is not engaging the corresponding taper on the screw head 30, thus allowing the screw head 30 to move freely. As shown in FIG. 8(B), the longitudinal member 50 is then dropped into the screw head 30 and rests on the saddle pin 40. At this point the saddle pin 40 is ready to deform to accept a larger size longitudinal member 50 than the slot 43 on top of the saddle pin 40 seems to accommodate.

Figure 8C:
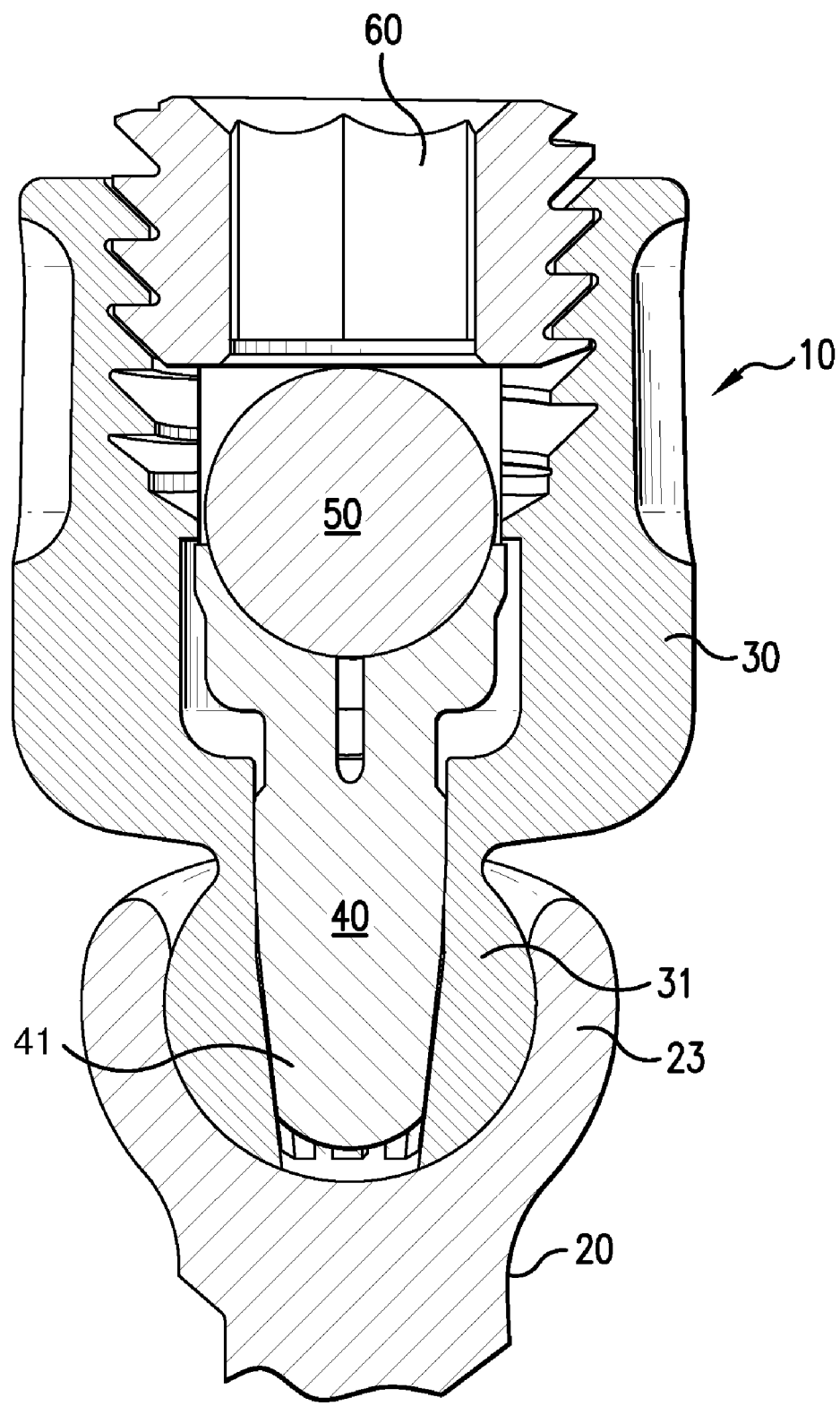
Figure 8D:
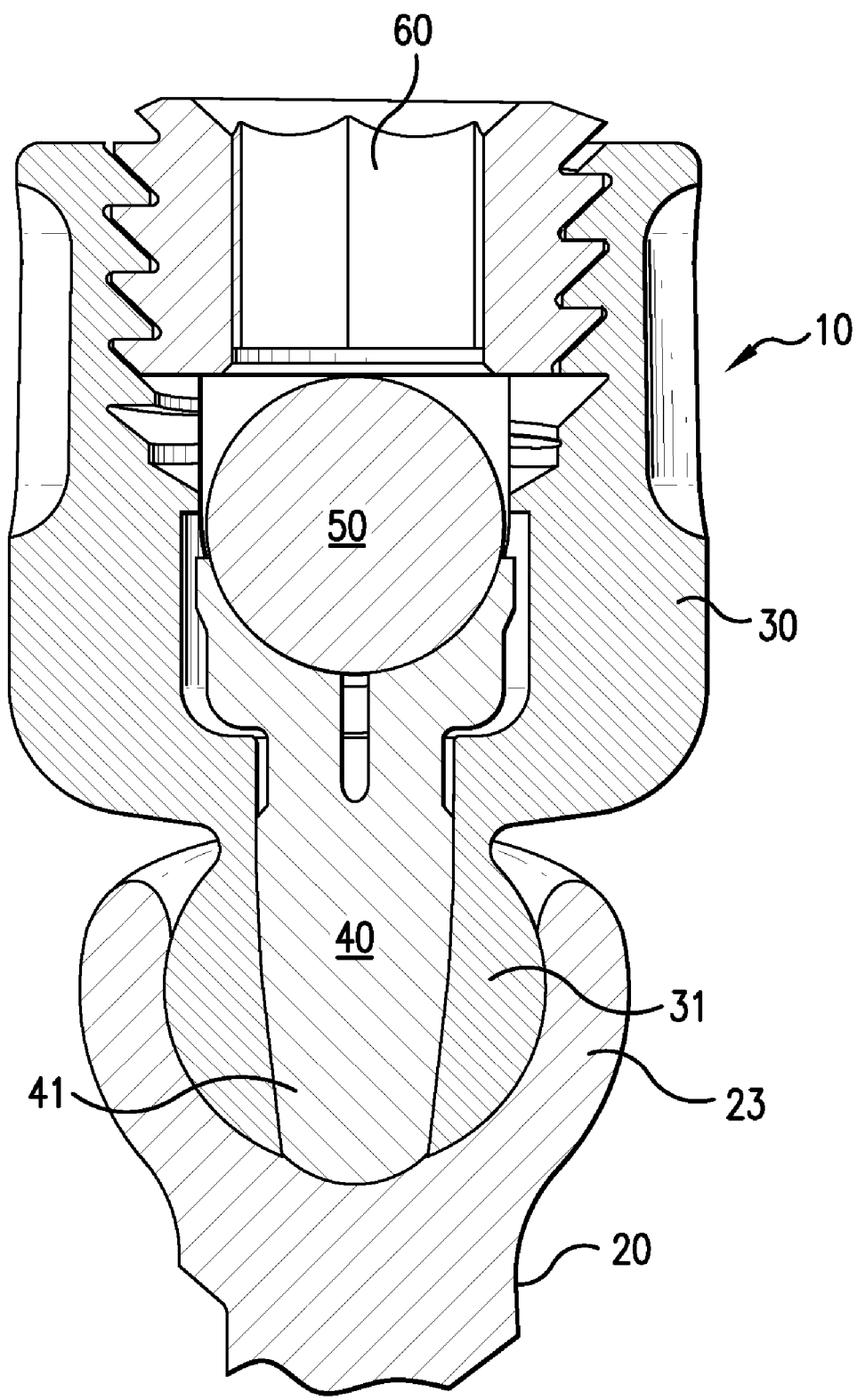
Figure 8E:
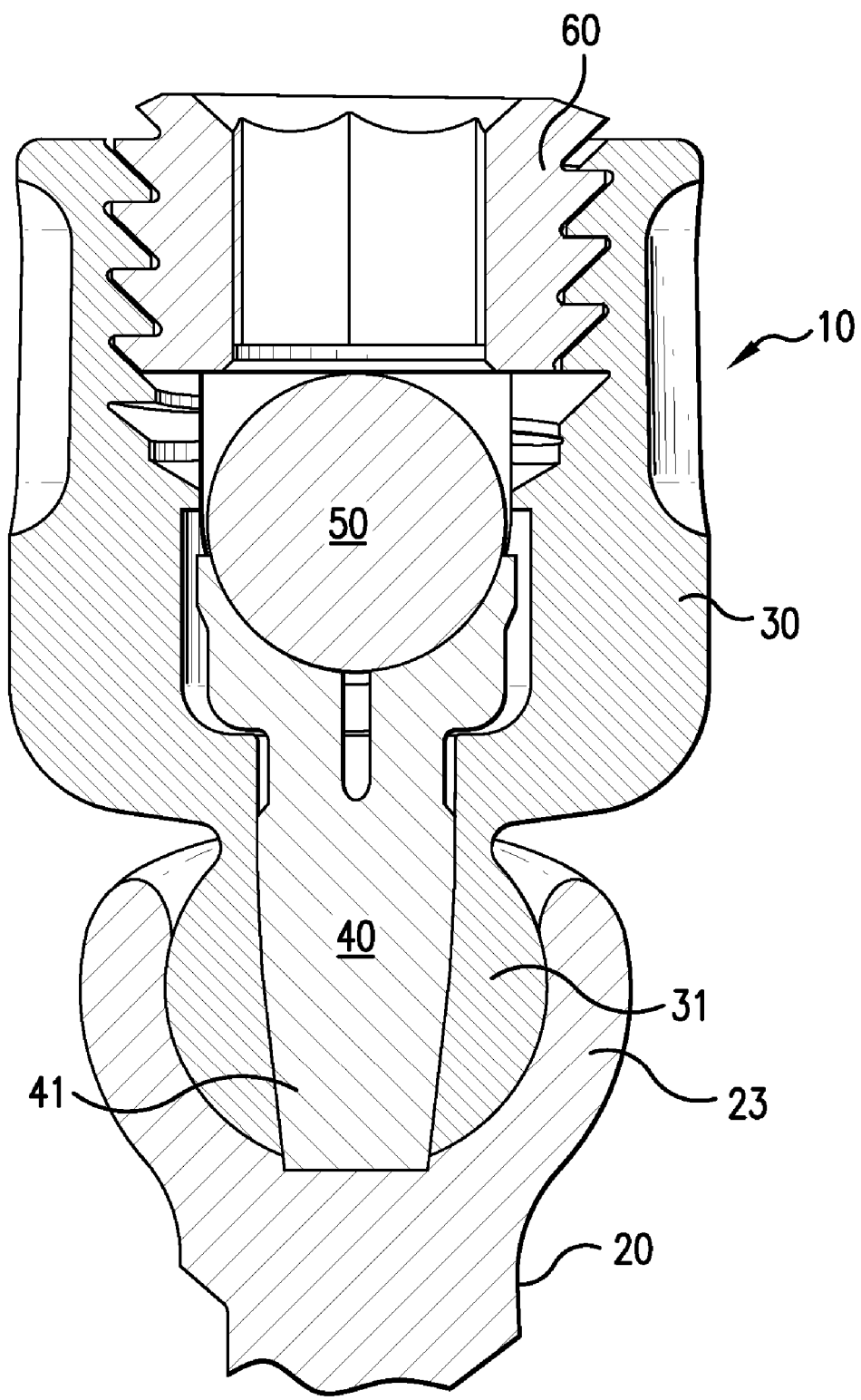

Next, as illustrated in FIG. 8(C), the blocker 60 is inserted into the screw head 30 preventing the longitudinal member 50 from escaping. The blocker 60 is now ready to apply downward forces on the saddle pin 40 through the longitudinal member 50. As shown in FIG. 8(D), the blocker 60 is fully tightened to a predetermined torque. The saddle pin 40 is driven into the bone fixator component 20 while expanding the bulbous end 31 of the screw head 30. The bulbous end 31 of the screw head 30 has very little room to expand. The wedging effect starts to lock the construct 10. FIG. 8(E) illustrates the assembly 10 in the locked position, whereby the saddle pin 40 has penetrated the bone fixator component 20 and "lifted" the male spherical portion 31 of the screw head 30 wedging it further into the socket 23 of the bone fixator component 20.

Figure 9B:
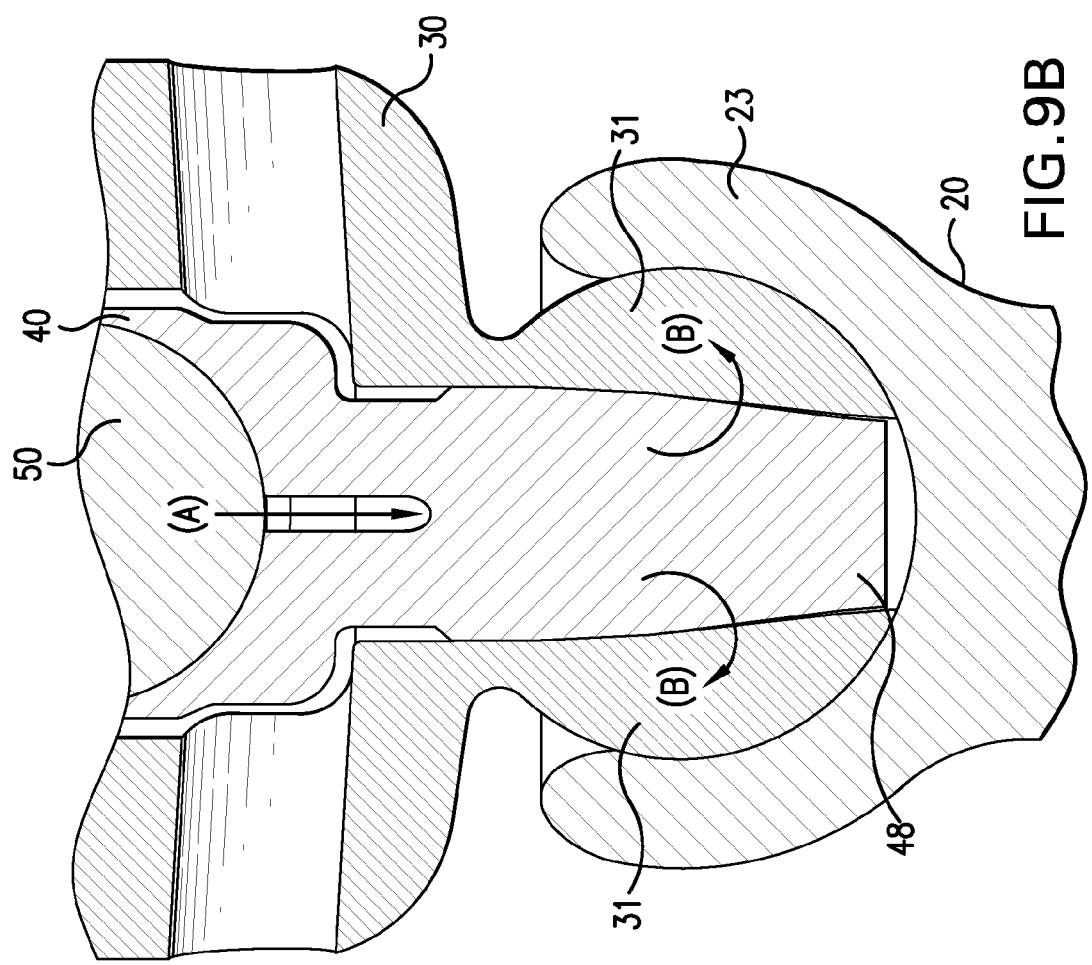

In terms of manufacturing the assembly 10, FIGS. 9(A) through 9(D) illustrate various sectional views of the assembly 10 and the corresponding forces acting upon the various components of the assembly 10 during the assembling process. Generally, the assembly 10 locks because of the engagement between the socket 23 of the bone fixator component 20 and the bulbous end 31 of screw head 30 from the force transmitted by the saddle pin 40 through the blocker 60 and the longitudinal member 50. The engaging system generally includes three stages: (1) before engaging (FIG. 9(A)); (2) start to engage (FIG. 9(B)); (3) fully engaged (FIGS. 9(C) and 9(D)). The performance of each component (bone fixator component 20, screw head 30, and saddle pin 50) varies per stage. As shown in FIG. 9(A) (before engaging), the saddle pin 40 has yet to transmit forces to the screw head 30 or to the bone fixator component 20. The saddle pin 40 sits in region R (denoted by the elliptical circles). In this stage, the saddle pin 40 has one direction of limited freedom, vertical.

As shown in FIG. 9(B), the saddle pin 40 starts to engage the bone screw 20. Force A is transmitted by the longitudinal member 50 and to the saddle pin 40 forcing the area of contact to increase accordingly. Enough contact force is generated to bend (denoted by force B) the male sphere 31 of the screw head 30. At this stage, the saddle pin 40 begins to contact the female socket 23 of the bone fixator component 20. As shown in FIG. 9(C), the saddle pin 40 is fully engaged. The blocker 60 pushes downward against the longitudinal member 50 and the saddle pin 40 and creates a force A. Force A is then separated into three forces: C, B, and $D_3$. Forces $D_3$ are pushing against the female socket 23 of the bone fixator component 20 thereby creating force E and driving the screw head 30 upward. By the screw head 30 moving upward, force $D_1$ is created. Finally, the locking mechanism is completed when forces $D_1$, $D_2$, and $D_3$ create a wedge between the screw head 30 and the bone fixator component 20 by working against forces C and E.

Figure 9D:
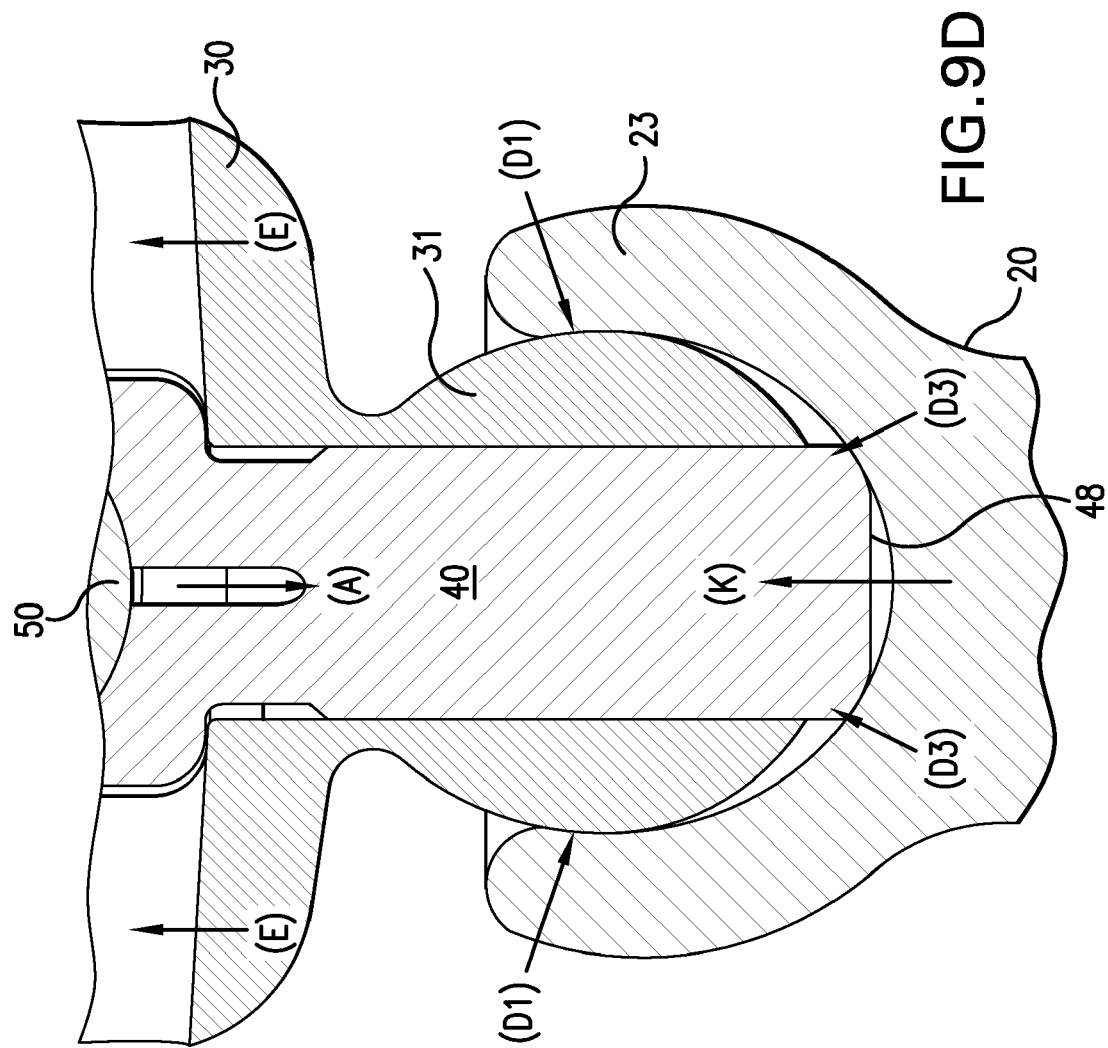

Since the major engaging component is executed by the forces $D_1$ and $D_3$, the above-described engaging method could be substituted by the following: bending forces B and the expansion forces C are ignored or removed. The forces $D_2$ are removed since the forces B and C are ignored or removed. Then, the contact forces $D_3$ are increased at the tip 48 of the saddle pin 40 and the forces $D_1$ acting on the opening of the bone fixator component 20. As such, FIG. 9(D) illustrates an alternative possibility of engaging the assembly 10. In this case, the force A is transmitting to the bone fixator component 20 and thereby creating the reaction forces $D_3$ or K, and depends on the shape of the tip 48 of the saddle pin 40. Again, forces $D_3$ or K are pushing against the female socket 23 of the bone fixator component 20, creating force E, and driving the screw head 30 upward. By the screw head 30 moving upward, force $D_1$ is created. Finally, the locking mechanism is completed when forces $D_1$ and $D_3$ (or K) created a wedge between the screw head 30 and the bone fixator component 20 by working against forces E.

Figure 10:
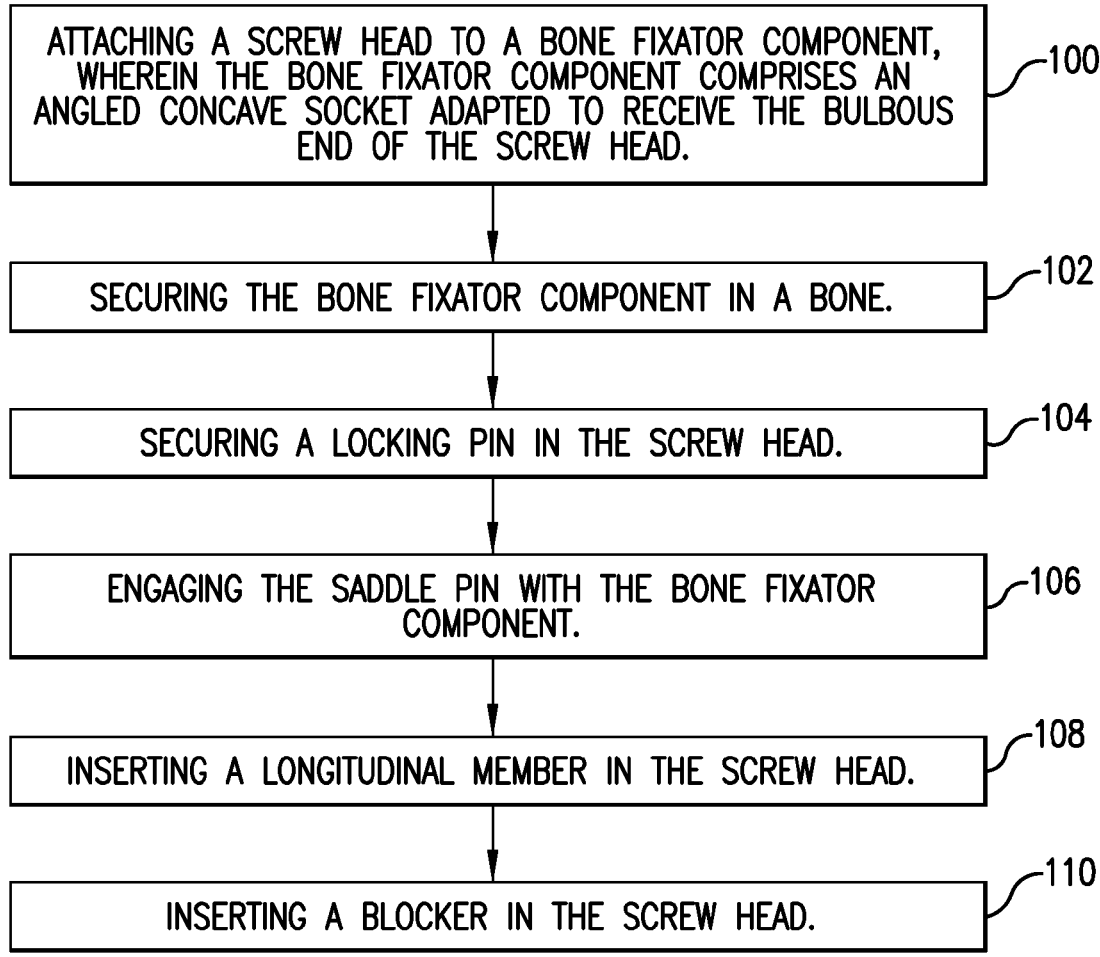
FIG. 10 is a flow diagram illustrating a preferred method according to an embodiment of the invention.

FIG. 10 (with reference to the components provided in FIGS. 1 through 9(D)) is a flow diagram illustrating a method of assembling a pedicle screw assembly 10, wherein the method preferably comprises attaching (100) a screw head 30 comprising a bulbous end 31 to a bone fixator component 20, wherein the bone fixator component 20 comprises an angled concave socket 23 adapted to receive the bulbous end 31 of the screw head 30; securing (102) the bone fixator component 20 in a bone; securing (104) a locking pin 40 in the screw head 30; engaging (106) the saddle pin 40 with the bone fixator component 20; inserting (108) a longitudinal member 50 in the screw head 30; and inserting (110) a blocker 60 in the screw head 30, wherein engagement of the blocker 60 with the screw head 30 causes expansion of the bulbous end 31 of the screw head 30 in the angled concave socket 23 of the bone fixator component 20.

Generally, as illustrated in FIGS. 1 through 5(B), the embodiments of the invention provide a pedicle screw assembly 10 comprising a screw head 30 comprising a bulbous end 31; a bone fixator component 20 comprising an angled top concave socket 23 adapted to receive the bulbous end 31 of the screw head 30; a pin 40 mounted in the screw head 30; and a blocker 60 adapted to engage the screw head 30. The screw head 30 comprises a slot 36 adapted to receive a longitudinal member 50. Moreover, the concave socket 23 of the bone fixator component 20 comprises a rounded bottom 26. Preferably, the concave socket 23 of the bone fixator component 20 comprises an inner portion 21 adapted to receive the bulbous end 31 of the screw head 30; and a dimpled 24 outer portion 25.

Additionally, the pin 40 is preferably adapted to engage the bone fixator component 20 and the longitudinal member 50, and the blocker 60 is preferably adapted to secure the longitudinal member 50. Preferably, the pin 40 comprises an upper saddle portion 42 having a slot 43 and a pair of upright ends 44, 45; and a lower tapered portion 47 adjacent to the slot 43. Preferably, the screw head 30 further comprises two opposed upright ends 34, 35 separated by the slot 36, wherein each of the opposed upright ends 34, 35 comprise an inner wall 134 and an outer wall 135, wherein the inner wall 134 comprises wall threads 37, and wherein the outer wall 135 comprises grooves 39.

Moreover, the blocker 60 preferably comprises blocker threads 61 configured around an outer perimeter 63 of the blocker 60, the blocker threads 61 being dimensioned and configured to mate with the wall threads 37 of the screw head 30. Furthermore, the bulbous end 31 of the screw head 30 may comprise a plurality of slots 32 terminating at an opening 138 at the tip 139 of the bulbous end 31. Also, the bulbous end 31 of the screw head 30 preferably comprises a hole 38 configured to receive the pin 40.

The embodiments of the invention offer a surgeon more lateral corrective distance than conventional screw assemblies and can accommodate the cervical spine anatomy with a biased angle. The embodiments of the invention may also be used as a fixation device in the posterior cervical-thoracic spine.

Additionally, the embodiments of the invention provide an improvement in the field of surgical lumbar and thoracic and cervical spine treatment. The assembly 10 provided by the embodiments of the invention may also be used anteriorly or posteriorly. Furthermore, the assembly 10 provided by the embodiments of the invention may be utilized in surgeries to achieve anterior lumbar interbody fusion, posterior lumbar interbody fusion, transverse lumbar interbody fusion, degenerative disc disease, adult and pediatric scoliosis as a fixation device, and posterior cervical fusion.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments of the invention have been described in terms of preferred embodiments, those skilled in the art will recognize that the embodiments of the invention can be practiced with modification within the spirit and scope of the appended claims.

What is claimed is:

1. A pedicle screw assembly comprising:
   a screw head comprising:
      an outwardly protruding and expandable bulbous end comprising a plurality of flanges and an inner portion, wherein said inner portion comprises a smooth-bored channel bored through said bulbous end;
      a slot adapted to receive a longitudinal member; and
      two opposed upright ends separated by said slot, wherein each of said opposed upright ends comprise an inner wall and an outer wall, wherein said inner wall comprises wall threads, and wherein said outer wall comprises grooves;
   a bone fixator component comprising an angled concave socket adapted to receive said bulbous end of said screw head;
   a pin mounted within an inner portion of said screw head and expanding said flanges of said bulbous end, wherein said pin sits flush with said slot and said pin sits flush with said smooth-bored channel; and
   a blocker adapted to engage said screw head and comprising blocker threads configured to mate with said wall threads.

2. The assembly of claim 1, wherein said concave socket comprises an angled top and a rounded bottom.

3. The assembly of claim 2, wherein said concave socket of said bone fixator component comprises:
   an upper outer surface adapted to allow said screw head to angulate in one direction more than another direction;
   an inner portion adapted to receive said bulbous end of said screw head; and
   a dimpled outer portion.

4. The assembly of claim 1, wherein said pin is adapted to engage said bone fixator component and said longitudinal member.

5. The assembly of claim 1, wherein said blocker is adapted to secure said longitudinal member.

6. The assembly of claim 1, wherein said pin comprises:
   an upper saddle portion having a slot and a pair of upright ends; and
   a lower tapered portion adjacent to said slot.

7. The assembly of claim 1, wherein said blocker threads are configured around an outer perimeter of said blocker.

8. The assembly of claim 1, wherein said bulbous end of said screw head comprises a plurality of slots terminating at an opening at a tip of said bulbous end.

9. The assembly of claim 1, wherein said bone fixator component comprises any of a bone screw and a hook.

10. A pedicle screw assembly comprising:
    a screw head comprising:
       an outwardly protruding and expandable bulbous end comprising a plurality of flanges and an inner portion, wherein said inner portion comprises a smooth-bored channel bored through said bulbous end;
       a slot adapted to receive a longitudinal member; and
       a plurality of opposed upright ends separated by said slot, wherein each of said opposed upright ends comprise an inner wall and an outer wall, wherein any of said inner wall and said outer wall comprises wall threads, and wherein any of said inner wall and said outer wall comprises grooves;
    a bone fixator component comprising a concave socket adapted to receive said bulbous end;
    a pin mounted within an inner portion of said screw head and expanding said flanges of said bulbous end, wherein said pin sits flush with said slot and said pin sits flush with said smooth-bored channel; and
    a blocker adapted to engage said screw head and comprising blocker threads configured to mate with said wall threads.

11. The assembly of claim 10, wherein said concave socket comprises an angled top and a rounded bottom.

12. The assembly of claim 11, wherein said concave socket of said bone fixator component comprises:
    an upper outer surface adapted to allow said screw head to angulate in one direction more than another direction;
    an inner portion adapted to receive said bulbous end of said screw head; and
    a dimpled outer portion.

13. The assembly of claim 10, wherein said pin is adapted to engage said bone fixator component and said longitudinal member.

14. The assembly of claim 10, wherein said blocker is adapted to secure said longitudinal member.

15. The assembly of claim 10, wherein said pin comprises:
    an upper saddle portion having a slot and a pair of upright ends; and
    a lower tapered portion adjacent to said slot.

16. The assembly of claim 10, wherein said blocker threads are configured around an outer perimeter of said blocker.

17. The assembly of claim 10, wherein said bulbous end of said screw head comprises:
    a plurality of slots terminating at an opening at a tip of said bulbous end.

18. A pedicle screw assembly comprising:
    a screw head comprising:
       an outwardly protruding and expandable bulbous component comprising a hole configured through a longitudinal axis of said bulbous component and a plurality of flanges, wherein said hole comprises a channel bored through said bulbous end;
       a slot comprising a longitudinal axis that is perpendicular to the longitudinal axis of said bulbous component; and
       opposed threaded upright ends separated by said slot;

a bone fixator component comprising a concave socket adapted to receive said bulbous component;

a pin mounted within an inner portion of said screw head and expanding said flanges of said bulbous end, wherein said pin sits flush with said slot and said pin sits flush with said channel; and a blocker adapted to engage said screw head and comprising blocker threads configured to mate with said threaded upright ends.

19. The assembly of claim 18, wherein said concave socket comprises:

an angled top comprising an upper outer surface adapted to allow said screw head to angulate in one direction more than another direction; and an inner portion adapted to receive said bulbous component.

* * * * *